(12) United States Patent
Kim et al.

(10) Patent No.: US 11,860,536 B2
(45) Date of Patent: Jan. 2, 2024

(54) THREE-DIMENSIONAL CROSSLINKER COMPOSITION AND METHOD OF MANUFACTURING ELECTRONIC DEVICES USING THE SAME

(71) Applicant: ULSAN NATIONAL INSTITUTE OF SCIENCE AND TECHNOLOGY, Ulsan (KR)

(72) Inventors: BongSoo Kim, Ulsan (KR); Myeong Jae Lee, Cheongju-si (KR)

(73) Assignee: UNIST (ULSAN NATIONAL INSTITUTE OF SCIENCE AND TECHNOLOGY), Ulsan (KR)

( * ) Notice: Subject to any disclaimer, the term of this patent is extended or adjusted under 35 U.S.C. 154(b) by 266 days.

(21) Appl. No.: 17/319,534

(22) Filed: May 13, 2021

(65) Prior Publication Data

US 2021/0397087 A1   Dec. 23, 2021

(30) Foreign Application Priority Data

Jun. 10, 2020   (KR) .................... 10-2020-0070392
Dec. 18, 2020   (KR) .................... 10-2020-0178860

(51) Int. Cl.
  G03F 7/008   (2006.01)
  C08G 61/02   (2006.01)
  (Continued)

(52) U.S. Cl.
  CPC .......... G03F 7/0085 (2013.01); C07C 247/18 (2013.01); C08G 61/02 (2013.01);
  (Continued)

(58) Field of Classification Search
  CPC ...... G03F 7/0085; G03F 7/2014; G03F 7/008; G03F 7/0046; H10K 50/11; H10K 10/488;
  (Continued)

(56) References Cited

U.S. PATENT DOCUMENTS 8,530,269 B2   9/2013   Chua et al.
9,176,380 B2   11/2015   Bowman et al.
(Continued)

FOREIGN PATENT DOCUMENTS

KR   10-2006-0030025 A   4/2006
KR   10-2019-0131823 A   11/2019
KR   20190131823 A   * 11/2019

OTHER PUBLICATIONS

Translated Application of Lee (Year: 2019).*
(Continued)

*Primary Examiner* — Mark F. Huff
*Assistant Examiner* — Andrew Preston Traywick
(74) *Attorney, Agent, or Firm* — Harness, Dickey & Pierce, P.L.C.

(57) ABSTRACT

The inventive concept relates to a three-dimensional crosslinker composition and a method of manufacturing an electronic device using the same. According to the inventive concept, the three-dimensional crosslinker composition may be represented by Formula 1 below.

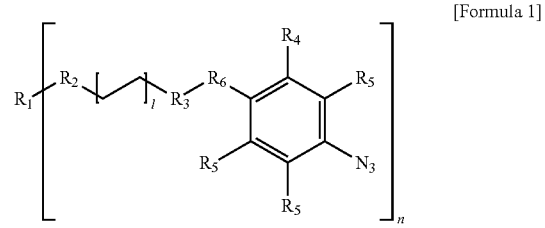

[Formula 1]

4 Claims, 14 Drawing Sheets

(51) Int. Cl.
    *C07C 247/18*     (2006.01)
    *H10K 71/20*     (2023.01)
    *H10K 10/46*     (2023.01)

(52) U.S. Cl.
    CPC ....... *H10K 71/233* (2023.02); *C07C 2601/16* (2017.05); *H10K 10/462* (2023.02)

(58) Field of Classification Search
    CPC ................ H10K 10/462; H10K 71/233; C07C 2601/16; C07C 247/18; C08G 61/02
    See application file for complete search history.

(56) References Cited

U.S. PATENT DOCUMENTS

| | | | |
|---|---|---|---|
| 9,745,252 | B2 | 8/2017 | Ho et al. |
| 9,847,220 | B2 | 12/2017 | Zhou et al. |
| 2007/0172978 | A1* | 7/2007 | Chua ............ H10K 71/10 438/99 |

OTHER PUBLICATIONS

Translated Description of Lee (Year: 2019).*
Office Action for Korean Application No. 10-2020-0178860 dated May 2, 2022.
R. Katritzky et al., "Triazole-oligomers by 1,3-dipolar cycloaddition", Issue in Honor of Prof. Edmunds Lukevics, 2006(v), p. 43-62.
Min Je Kim et al., "Universal three-dimensional crosslinker for allphotopatterned electronics", Nature Communications | (2020) 11:1520.
Min Je Kim et al., "Universal Three-Dimensional Crosslinker for All-Photopatterned Electronics" p. 1-28.
Rui-Qi Png et al., "High-performance polymer semiconducting heterostructure devices by nitrene-mediated photocrosslinking of alkyl side chains", Nature Materials, vol. 9, Feb. 2010.
"Supplementary S1: Synthesis of photo-crosslinker", Nature Materials Supplementary Information doi:10.1038/nmat2594.

* cited by examiner

THREE-DIMENSIONAL CROSSLINKER COMPOSITION AND METHOD OF MANUFACTURING ELECTRONIC DEVICES USING THE SAME

CROSS-REFERENCE TO RELATED APPLICATIONS

This U.S. non-provisional patent application claims priority under 35 U.S.C. § 119 of Korean Patent Application Nos. 10-2020-0070392, filed on Jun. 10, 2020, and 10-2020-0178860, filed on Dec. 18, 2020, the entire contents of which are hereby incorporated by reference.

BACKGROUND

The present disclosure herein relates to a crosslinker composition, and more particularly, to a three-dimensional crosslinker composition used for the manufacture of an electronic device.

A method of manufacturing an electronic device by a solution process is innovative technology having advantages in significantly reducing processing costs than a method of manufacturing an electronic device by the conventional vacuum-based process. However, technique for patterning each material layer by a solution process using materials used for the manufacture of an electronic device generally uses a photosensitive resin and requires an etching process. Accordingly, a method of manufacturing an electronic device by the conventional solution process may be complicated, and there are problems in that materials to be patterned may be damaged. Particularly, when manufacturing an upper layer in a patterning process of a material layer through a solution process, a lower layer may be damaged and the deteriorating phenomenon of the electrical device properties is generated. These problems come to the fore when manufacturing a large-area array electronic device or circuit as well as a single device.

SUMMARY

The present disclosure provides a crosslinker composition used for the manufacture of an electronic device and a method of manufacturing an electronic device using the same.

The tasks to solve in the present disclosure are not limited to the aforementioned tasks, and unmentioned other tasks may be clearly understood by a person skilled in the art from the description below.

An embodiment of the inventive concept relates to a crosslinker composition including a compound represented by Formula 1 below.

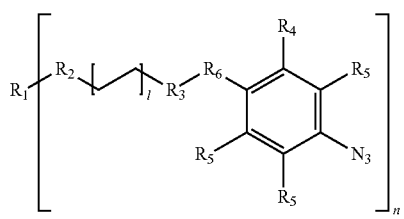

[Formula 1]

An embodiment of the inventive concept relates to a crosslinker composition including a compound represented by Formula 2 below.

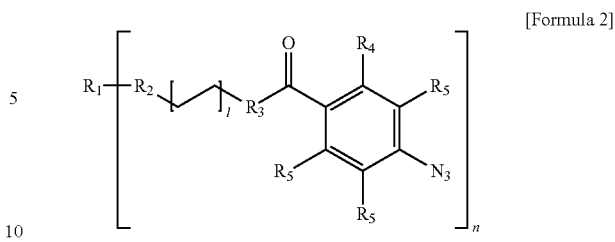

[Formula 2]

An embodiment of the inventive concept relates to a method of manufacturing an electronic device, including applying a crosslinker composition represented by Formula 1 below on a substrate to form a lower layer, and patterning the lower layer.

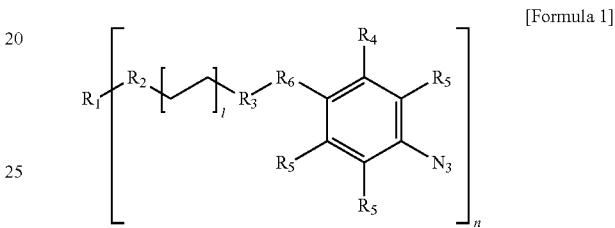

[Formula 1]

BRIEF DESCRIPTION OF THE FIGURES

The accompanying drawings are included to provide a further understanding of the inventive concept and are incorporated in and constitute a part of this specification. The drawings illustrate embodiments of the inventive concept and, together with the description, serve to explain principles of the inventive concept. In the drawings.

DETAILED DESCRIPTION

Figure 1:
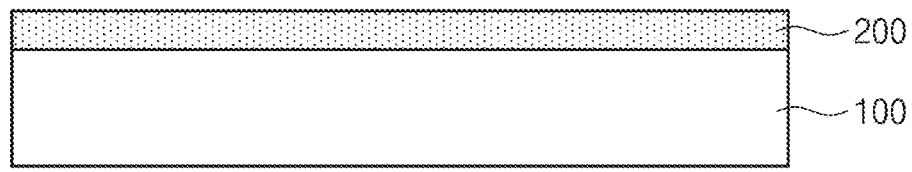
FIG. 1 to FIG. 3 are cross-sectional views for explaining a method of manufacturing an electronic device using a crosslinker composition according to embodiments of the inventive concept.

Preferred embodiments of the inventive concept will be described with reference to the accompanying drawings for sufficient understanding of the configuration and effects of the present disclosure. The inventive concept may, however, be embodied in various forms and diverse changes and should not be constructed as limited to the embodiments set forth herein. Rather, these embodiments are provided so that this disclosure will be thorough and complete, and will fully convey the scope of the inventive concept to those skilled in the art. A person skilled in the art might understand that the inventive concept may be conducted under what kind of suitable environment.

The terms used in the disclosure are for explaining embodiments but are not intend to limit the present disclosure. In the disclosure, the singular forms are intended to include the plural forms as well, unless the context clearly indicates otherwise. It will be further understood that the terms "comprises" and/or "comprising," when used in this specification, specify the presence of stated materials, elements, steps, operations, and/or devices, but do not preclude the presence or addition of one or more other materials, elements, steps, operations, and/or devices.

In the disclosure, an alkyl group may be a linear alkyl group, a branched alkyl group, or a cyclic alkyl group. The carbon number of the alkyl group is not specifically limited but may be an alkyl group of 1 to 30 carbon atoms. Examples of the alkyl group may include a methyl group, an ethyl group, an n-propyl group, an isopropyl group, an n-butyl group, a t-butyl group, an i-butyl group, a 2-ethylbutyl group, a 3,3-dimethylbutyl group, an n-pentyl group, an i-pentyl group, a neopentyl group, a t-pentyl group, and a cyclopentyl group, but an embodiment of the inventive concept is not limited thereto.

In the disclosure, the carbon number of an alkoxy group is not specifically limited but may be 1 to 30. The alkoxy group may include an alkyl alkoxy group and an aryl alkoxy group.

In the disclosure, the alkenyl group may be a linear alkenyl group or a branched alkenyl group. The carbon number of the alkenyl group is not specifically limited but may be 1 to 30. Examples of the alkenyl group may include a vinyl group, a 1-butenyl group, a 1-pentenyl group, a 1,3-butadienyl aryl group, a styrenyl group, and a styrylvinyl group, but an embodiment of the inventive concept is not limited thereto. In addition, in the disclosure, the alkenyl group may include an allyl group.

In the disclosure, a hydrocarbon ring includes an aliphatic hydrocarbon ring and an aromatic hydrocarbon ring. The hydrocarbon ring may be a monocycle or a polycycle. A heterocycle includes an aliphatic heterocycle and an aromatic heterocycle. The heterocycle may be a monocycle or a polycycle.

In the disclosure, examples of the halogen may include fluorine (F), chlorine (Cl), bromine (Br), and iodine (I), but an embodiment of the inventive concept is not limited thereto.

In the disclosure, the term "substituted or unsubstituted" corresponds to substituted or unsubstituted with one or more substituents selected from the group consisting of a hydrogen atom, a deuterium atom, a halogen atom, a hydroxyl group, an alkoxy group, an ether group, a halogenated alkyl group, a halogenated alkoxy group, a halogenated ether group, an alkyl group, an alkenyl group, an aryl group, a hydrocarbon ring group and a heterocyclic group. In addition, each of the substituents may be substituted or unsubstituted. For example, the halogenated alkoxy group may be construed as the alkoxy group.

In the disclosure, in case of not drawing a chemical bond at a position where a chemical bond is required, it means that a hydrogen atom is bonded at that position, unless otherwise defined.

In the disclosure, like reference numerals refer to like elements throughout.

Hereinafter, in order to explain the inventive concept more particularly, embodiments according to the inventive concept will be explained in more detail with reference to attached drawings.

Figure 2:
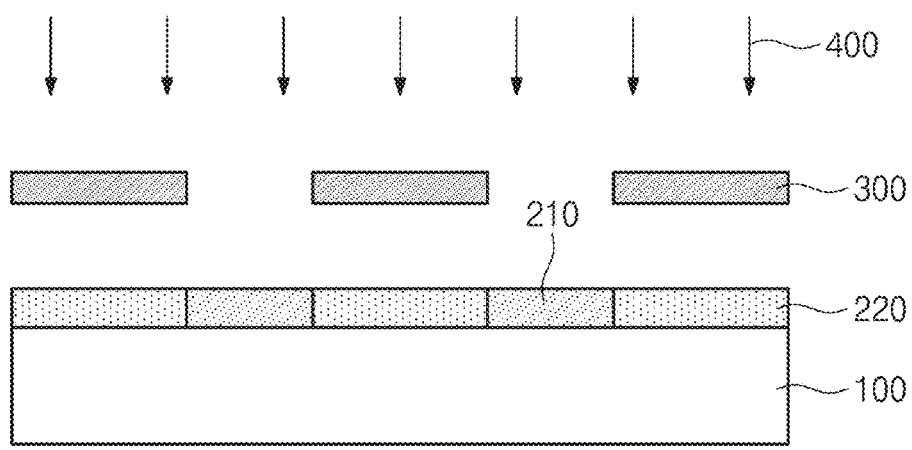
Figure 3:
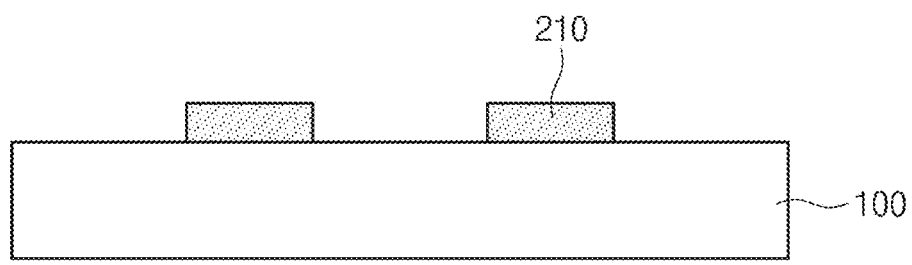

FIG. 1 to FIG. 3 are cross-sectional views for explaining a method of manufacturing an electronic device using a crosslinker composition according to embodiments of the inventive concept.

Referring to FIG. 1, a substrate 100 may be provided. On the substrate 100, a lower layer 200 may be formed. For example, the formation of the lower layer 200 may be performed by spin coating. The lower layer 200 may be a single layer or a stacked multiple layers. Though not shown, layers may be further provided between the substrate 100 and the lower layer 200. The lower layer 200 may be an etching target layer. The lower layer 200 may include any one among a semiconductor material (for example, organic semiconductor material), a metal material (for example, metal nanoparticle and/or quantum dot nanoparticle), and an insulating material (for example, polymer insulating material).

The semiconductor material may include a polymer or an organic semiconductor material. For example, the semiconductor material may include at least one among P(DPP2DT-TVT), P(DPP2DT-T2), P(DPP2DT-F2T2), P(DPP2DT-TT), P(NDI3OT-Se2), P(NDI3OT-Se), and P(NDI2OD-Se2). However, these are only illustrations, and an embodiment of the inventive concept is not limited thereto.

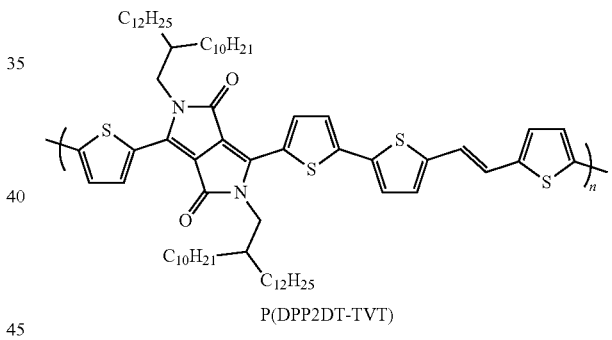

P(DPP2DT-TVT)

P(DPP2DT-T2)

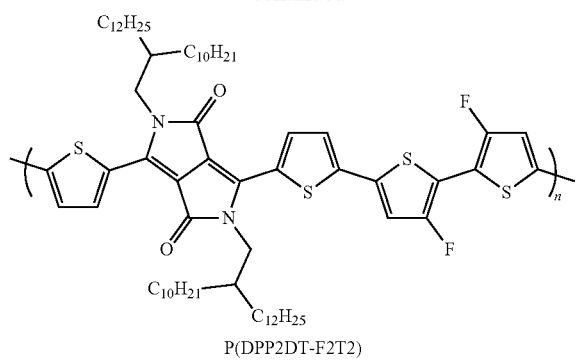

P(DPP2DT-F2T2)

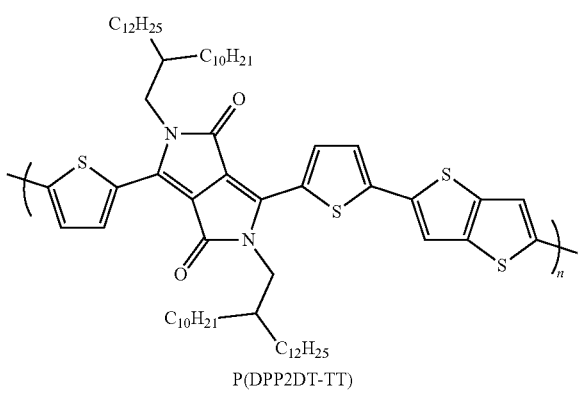

P(DPP2DT-TT)

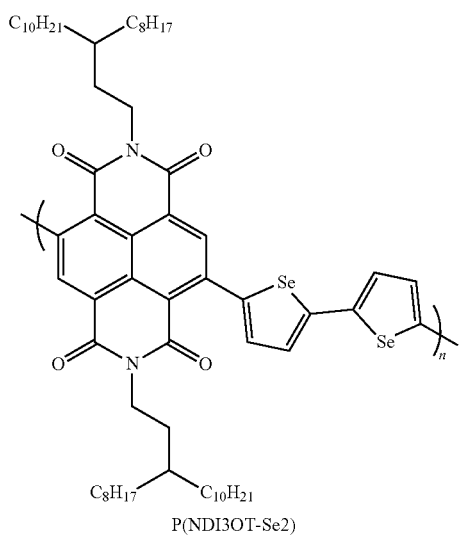

P(NDI3OT-Se2)

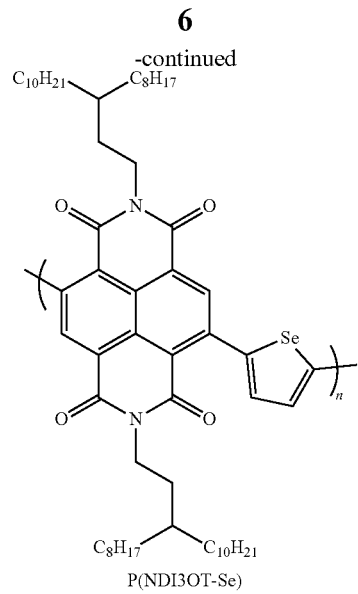

P(NDI3OT-Se)

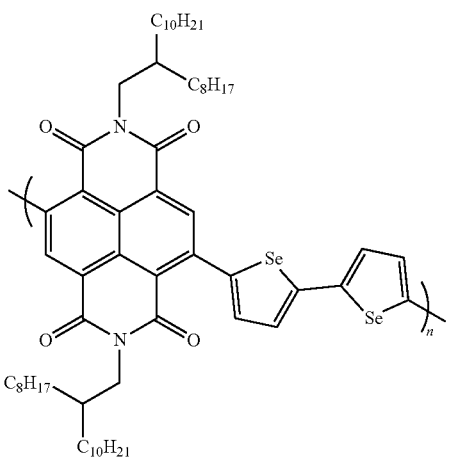

P(NDI2OD-Se2)

In an embodiment, the polymer insulating material may include at least one among PMMA, PS and PVDF-HFP.

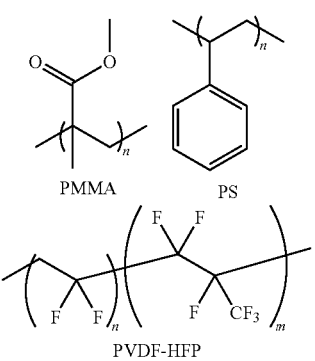

PMMA    PS

PVDF-HFP

In an embodiment, the metal nanoparticle may include a metal nanoparticle such as a silver nanoparticle (AgNP) and a gold nanoparticle (AuNP). However, these are only illustrations, and an embodiment of the inventive concept is not limited thereto.

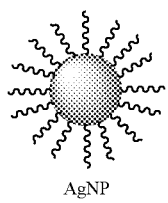

AgNP

In addition, the lower layer 200 may include a crosslinker composition. The crosslinker composition may have a three-dimensional structure. The concentration of the crosslinker composition may be about 0.1 wt % to about 50 wt %, more preferably, about 0.1 wt % to about 5 wt %. According to some embodiments of the inventive concept, the crosslinker composition may be represented by Formula 1 below.

[Formula 1]

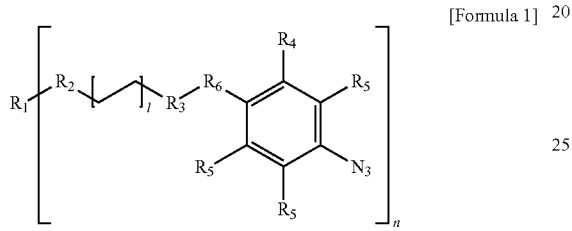

In Formula 1, $R_1$ is a linear type or branch type alkyl group of $C_1$ to $C_{30}$, or a linear type or branch type alkoxy group of $C_1$ to $C_{30}$, $R_2$ is O, S, NH, $CH_2$ or

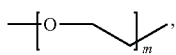, $R_3$ is O, S, NH or $CH_2$, $R_4$ is hydrogen, halogen, a linear type or branch type alkyl group of $C_1$ to $C_{30}$, a linear type or branch type alkoxy group of $C_1$ to $C_{30}$, a linear type or branch type alkyl group of $C_1$ to $C_{30}$, where at least one hydrogen is substituted with halogen, or a linear type or branch type alkoxy group of $C_1$ to $C_{30}$, where at least one hydrogen is substituted with halogen, $R_5$ is hydrogen or halogen, $R_6$ is CO, $CH_2$, or $SO_2$, "l" and "m" are each independently an integer of 1 to 30, and "n" is an integer of 3 to 12.

The halogen may include F or Cl.

For example, $R_4$ may include any one selected among Formula R-1 to Formula R-97 below.

Formula R-1

Formula R-2

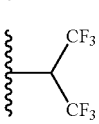

Formula R-3

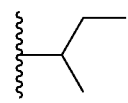

Formula R-4

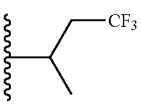

Formula R-5

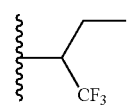

Formula R-6

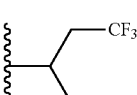

Formula R-7

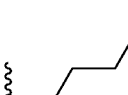

Formula R-8

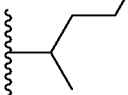

Formula R-9

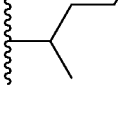

Formula R-10

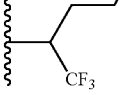

Formula R-11

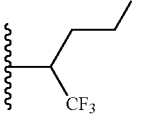

Formula R-12

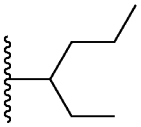

Formula R-13

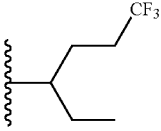

Formula R-14

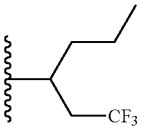

Formula R-15

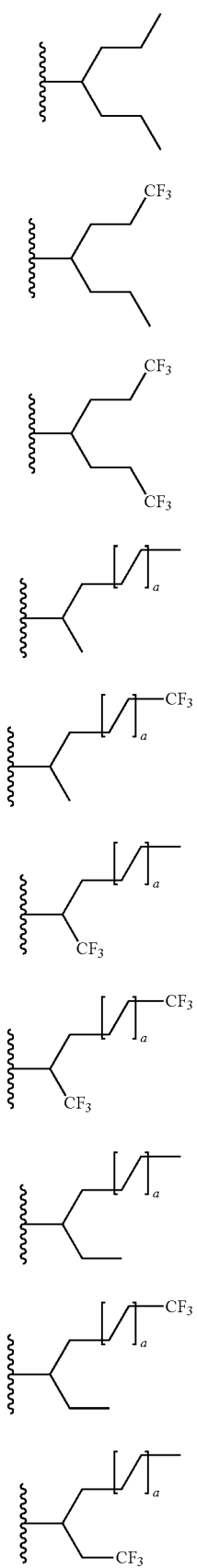
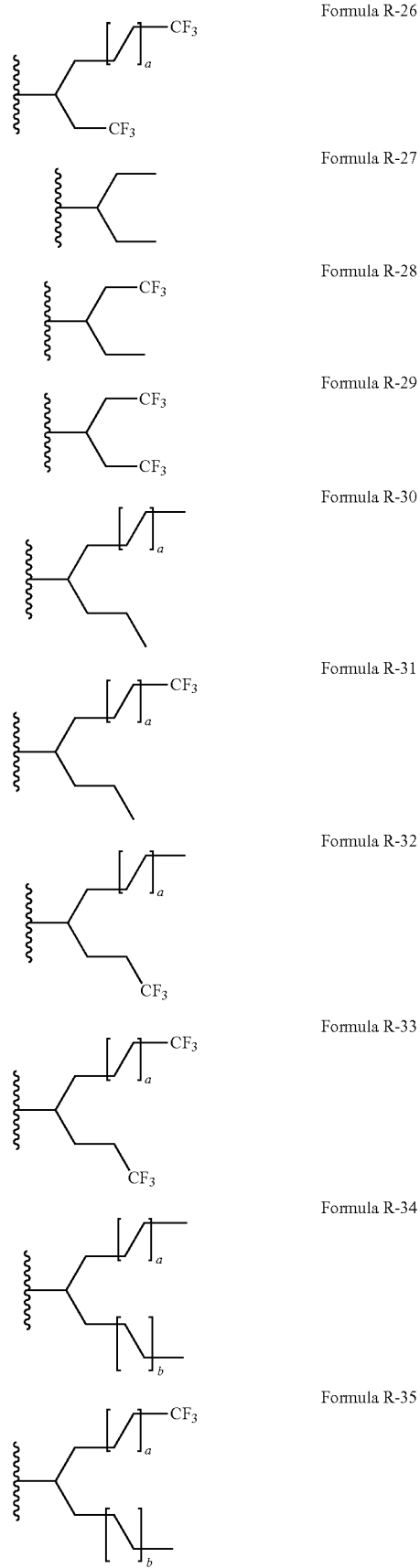

Formula R-36
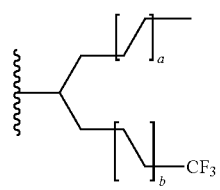
Formula R-37
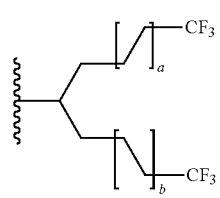
Formula R-38
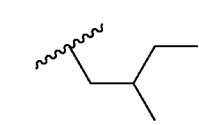
Formula R-39
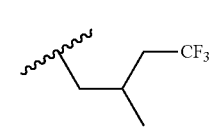
Formula R-40
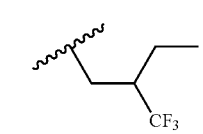
Formula R-41
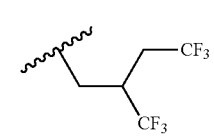
Formula R-42
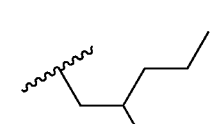
Formula R-43
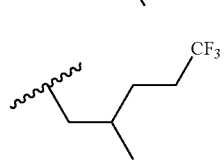
Formula R-44
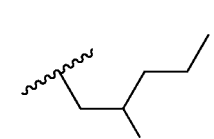
Formula R-45
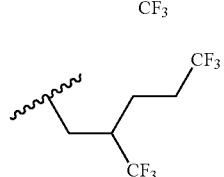
Formula R-46
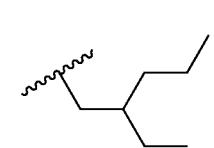
Formula R-47
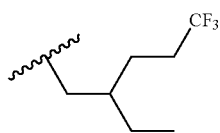
Formula R-48
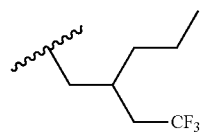
Formula R-49
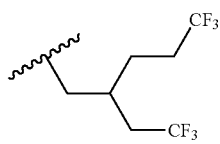
Formula R-50
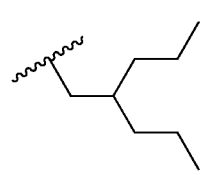
Formula R-51
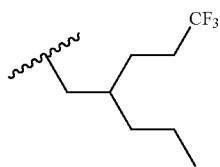
Formula R-52
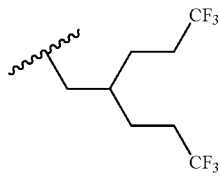
Formula R-53
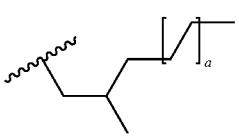
Formula R-54
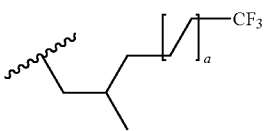
Formula R-55
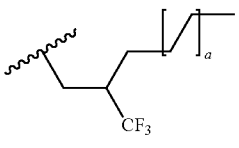
Formula R-56
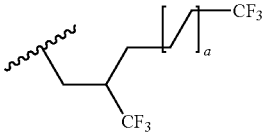

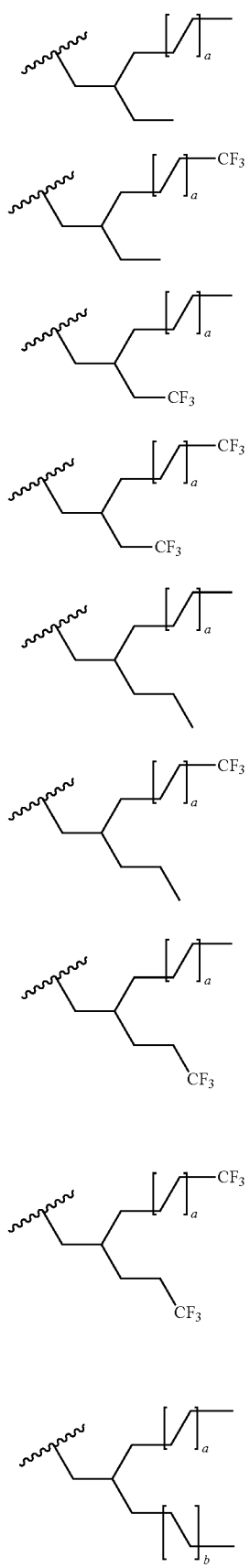
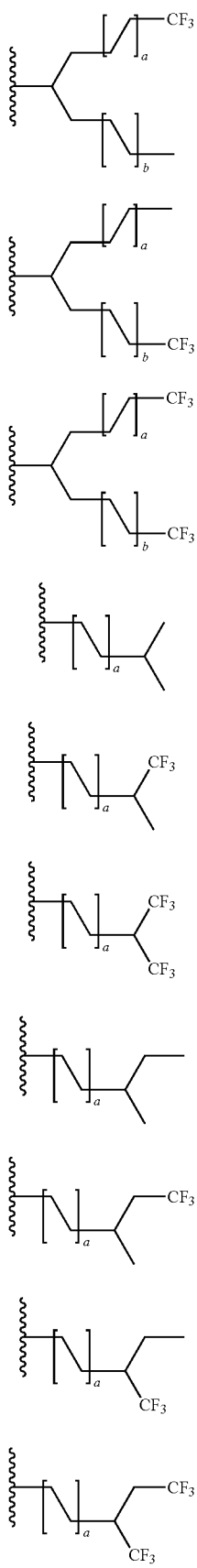
Formula R-57
Formula R-58
Formula R-59
Formula R-60
Formula R-61
Formula R-62
Formula R-63
Formula R-64
Formula R-65
Formula R-66
Formula R-67
Formula R-68
Formula R-69
Formula R-70
Formula R-71
Formula R-72
Formula R-73
Formula R-74
Formula R-75

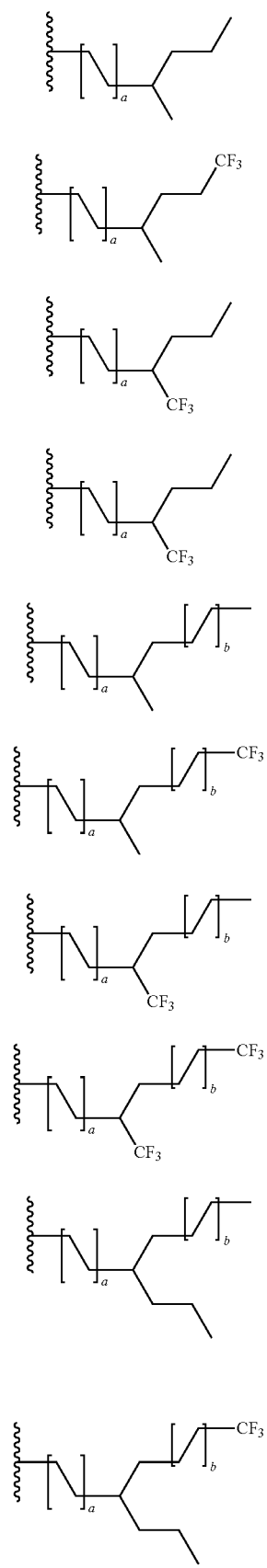
Formula R-76
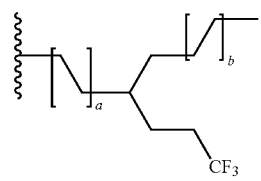
Formula R-77
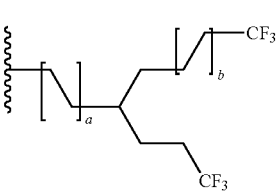
Formula R-78
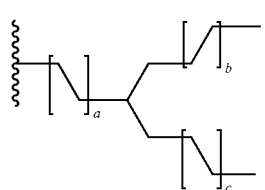
Formula R-79
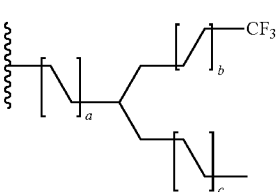
Formula R-80
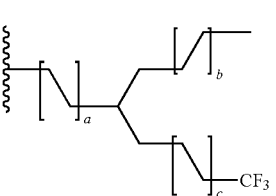
Formula R-81
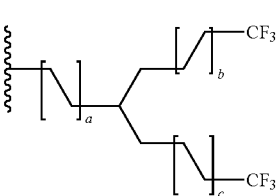
Formula R-82
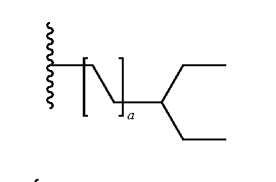
Formula R-83
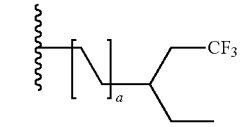
Formula R-84
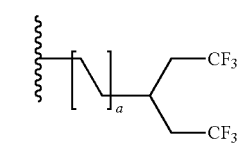
Formula R-85

-continued
Formula R-95
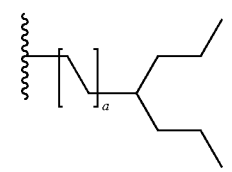
Formula R-96
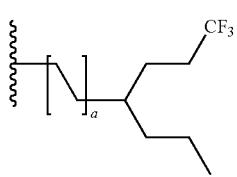
-continued
Formula R-97
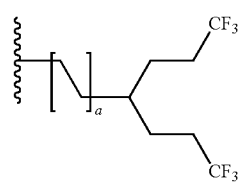
In Formula R-1 to Formula R-97, "a", "b" and "c" are each independently an integer of 1 to 30.
The compound represented by Formula 1 may include any one selected from Formula 1-1 to Formula 1-6 below.
[Formula 1-1]
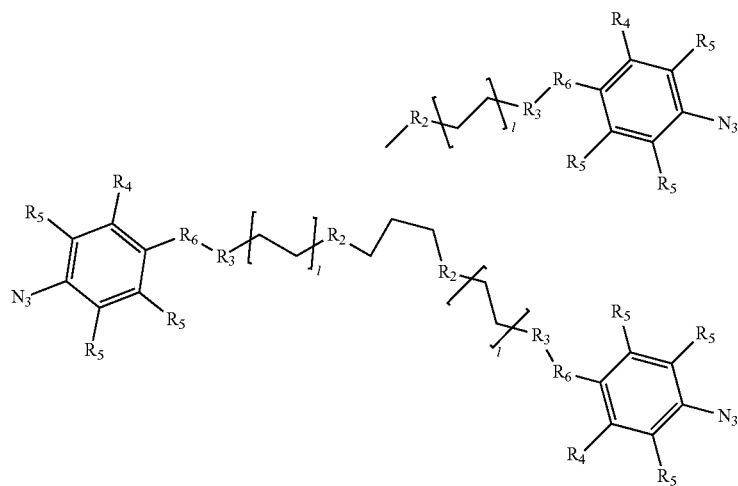
[Formula 1-2]
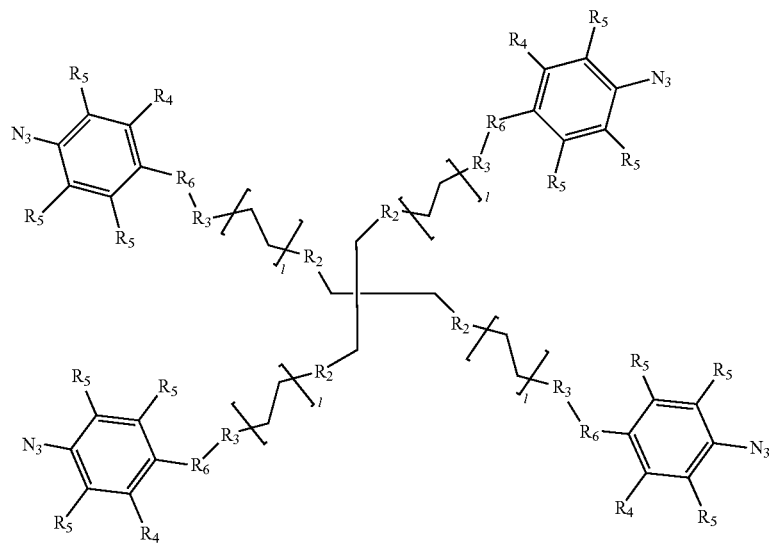

[Formula 1-3]
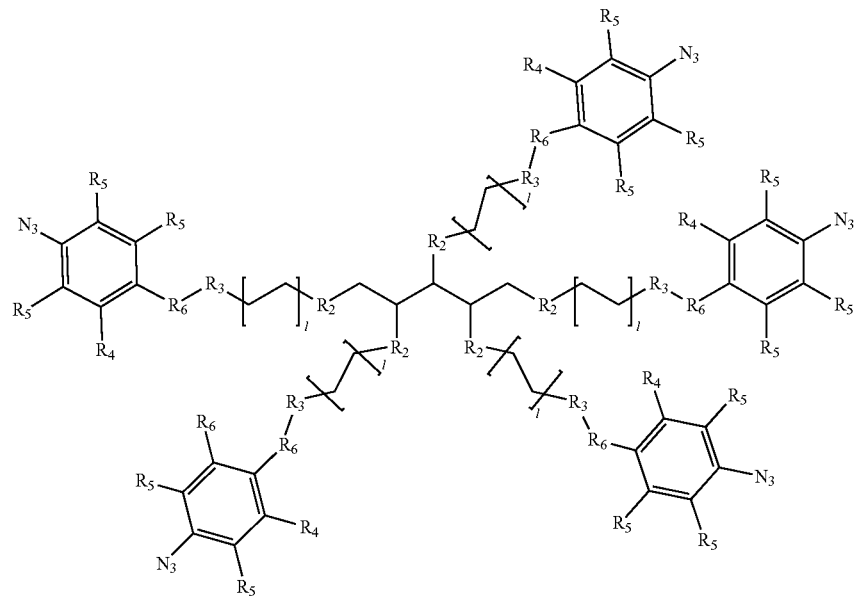
[Formula 1-4]
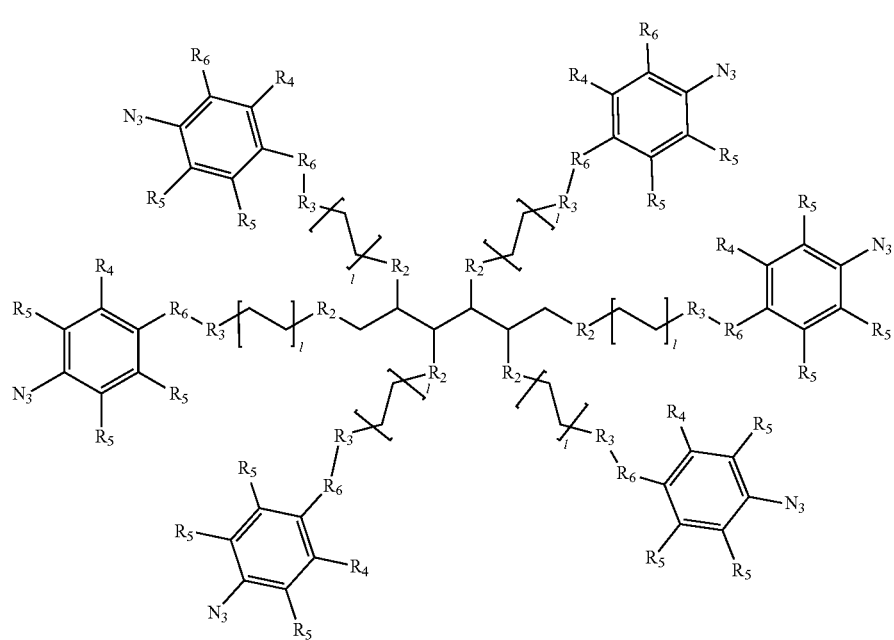

[Formula 1-5]
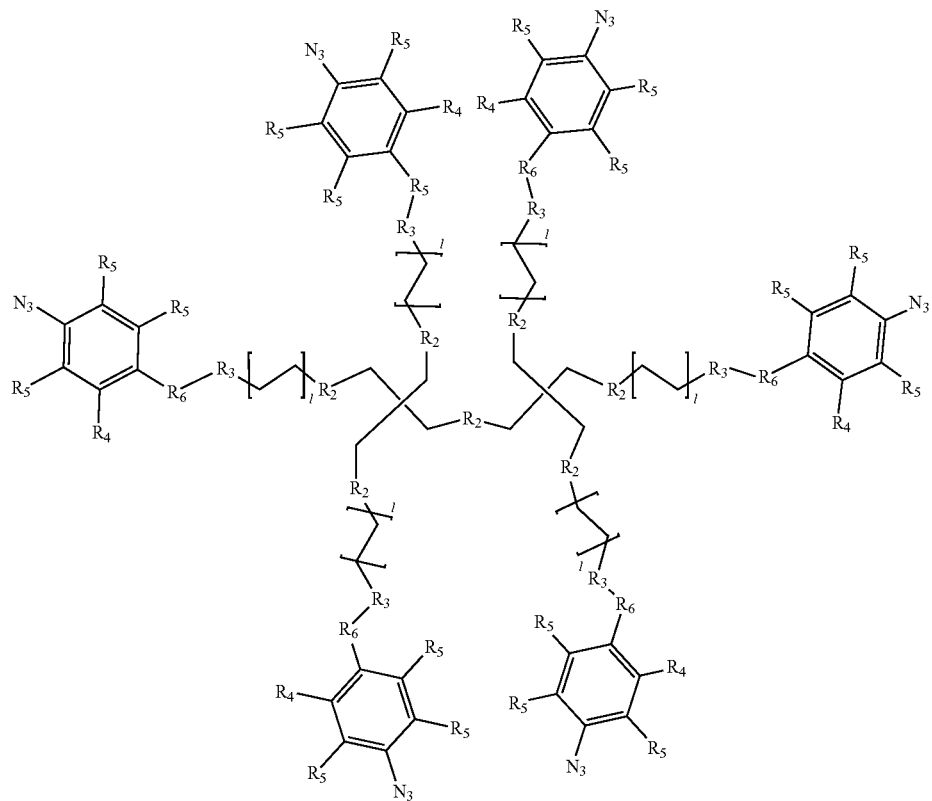
[Formula 1-6]
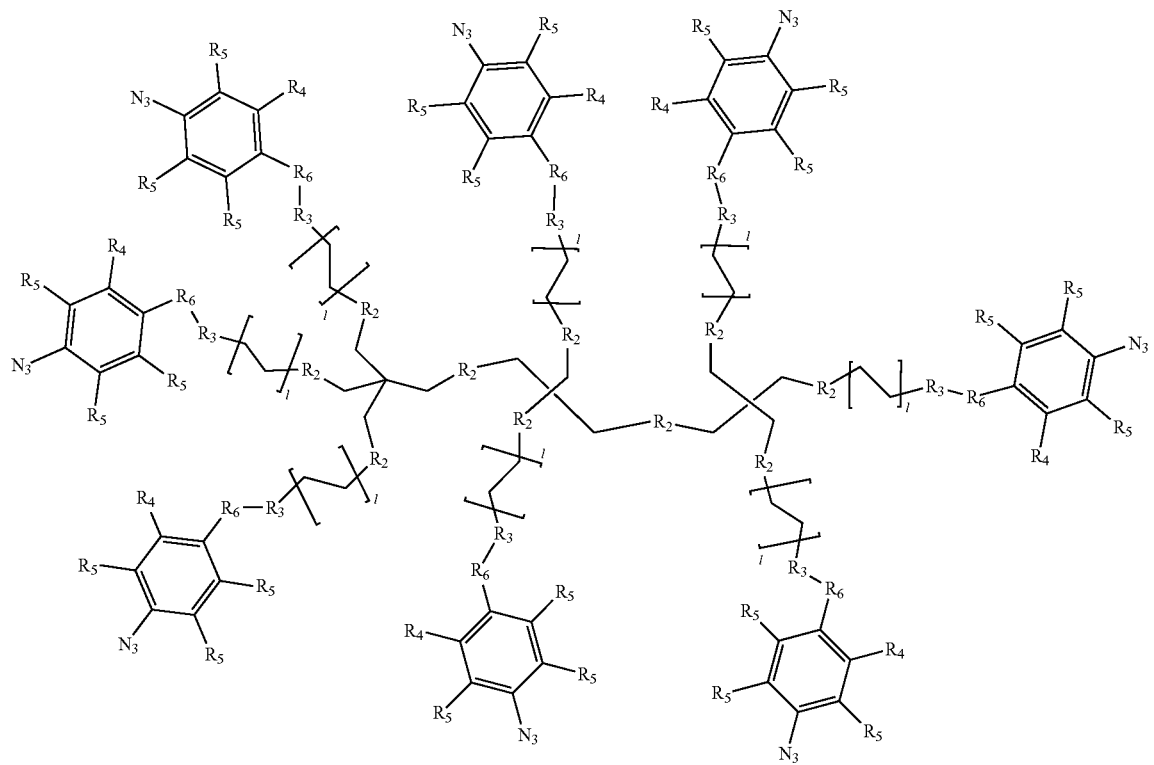

In Formula 1-1 to Formula 1-6, $R_2$ is O, S, NH, $CH_2$ or

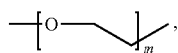

$R_3$ is O, S, NH or $CH_2$, $R_4$ is hydrogen, halogen, a linear type or branch type alkyl group of $C_1$ to $C_{30}$, a linear type or branch type alkoxy group of $C_1$ to $C_{30}$, a linear type or branch type alkyl group of $C_1$ to $C_{30}$, where at least one hydrogen is substituted with halogen, or a linear type or branch type alkoxy group of $C_1$ to $C_{30}$, where at least one hydrogen is substituted with halogen, $R_5$ is hydrogen or halogen, $R_6$ is CO, $CH_2$, or $SO_2$, and "l" and "m" are each independently an integer of 1 to 30.

In some embodiments of the inventive concept, the crosslinker composition may be represented by Formula 2 below.

[Formula 2]

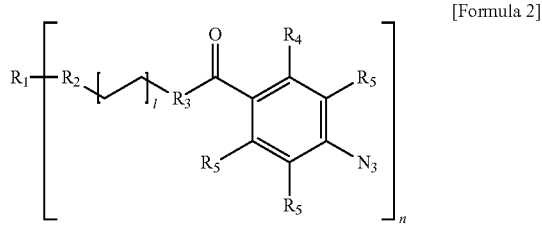

In Formula 2, $R_1$ is a linear type or branch type alkyl group of $C_1$ to $C_{30}$, or a linear type or branch type alkoxy group of $C_1$ to $C_{30}$, $R_2$ is O, S, NH, $CH_2$ or

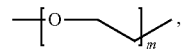

$R_3$ is O, S, NH or $CH_2$, $R_4$ is hydrogen, halogen, a linear type or branch type alkyl group of $C_1$ to $C_{30}$, a linear type or branch type alkoxy group of $C_1$ to $C_{30}$, a linear type or branch type alkyl group of $C_1$ to $C_{30}$, where at least one hydrogen is substituted with halogen, or a linear type or branch type alkoxy group of $C_1$ to $C_{30}$, where at least one hydrogen is substituted with halogen, $R_5$ is hydrogen or halogen, "l" and "m" are each independently an integer of 1 to 30, and "n" is an integer of 3 to 12.

The halogen may include F or Cl.

For example, $R_4$ may include any one selected among Formula R-1 to Formula R-97 above.

The compound represented by Formula 2 may include any one selected from Formula 2-1 to Formula 2-6 below.

[Formula 2-1]

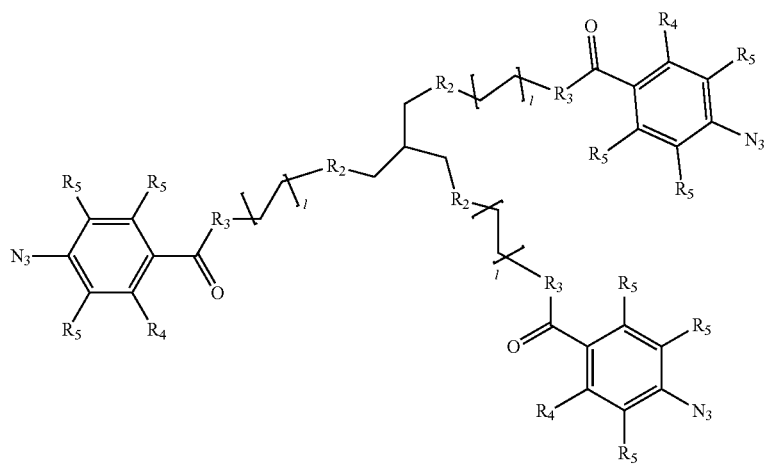

[Formula 2-2]
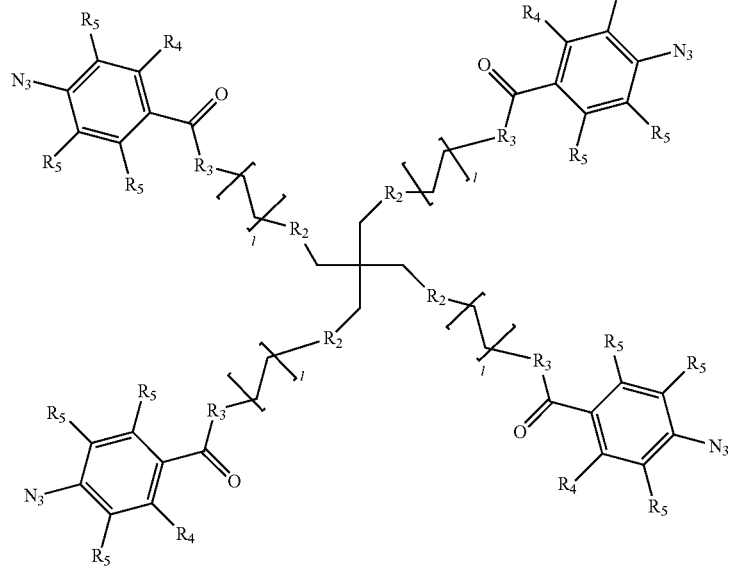
[Formula 2-3]
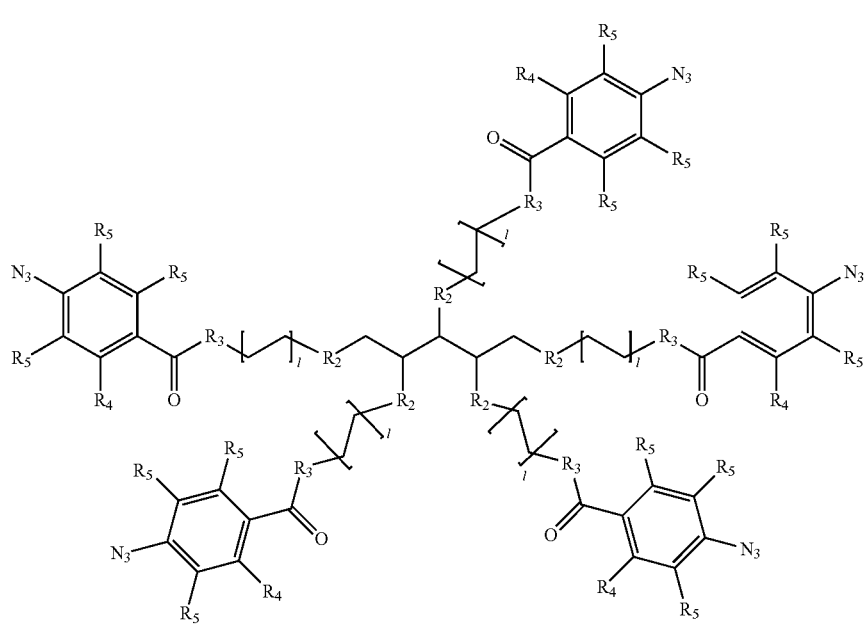

[Formula 2-4]
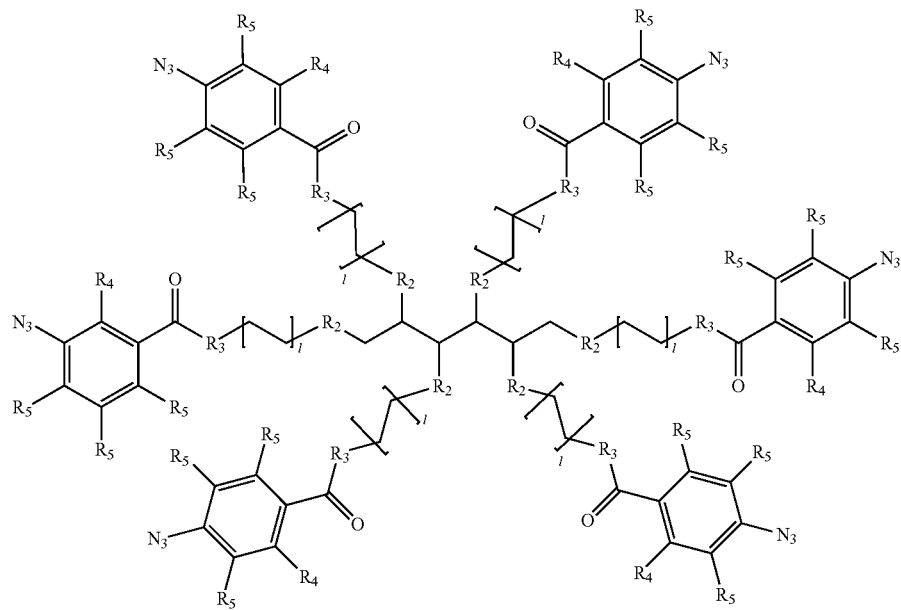
[Formula 2-5]
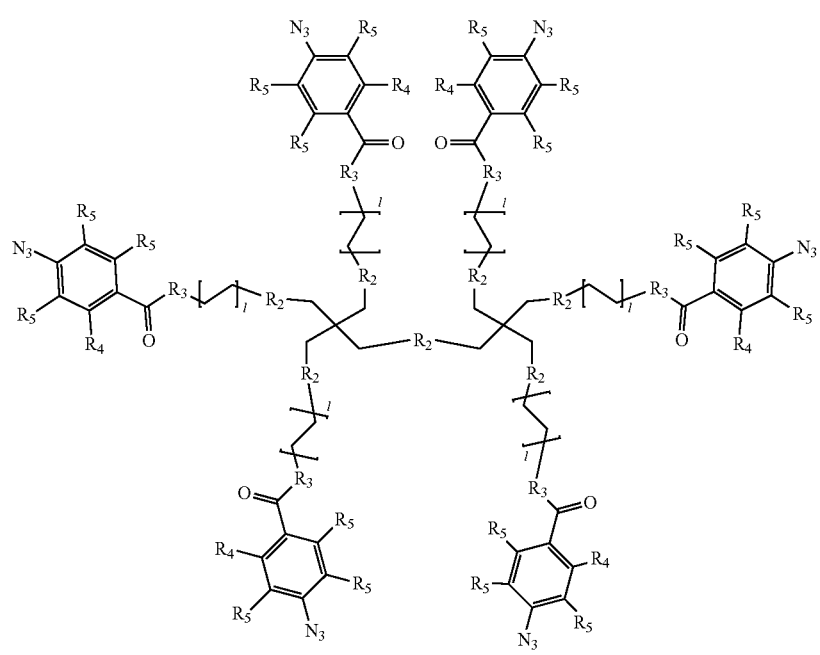

[Formula 2-6]

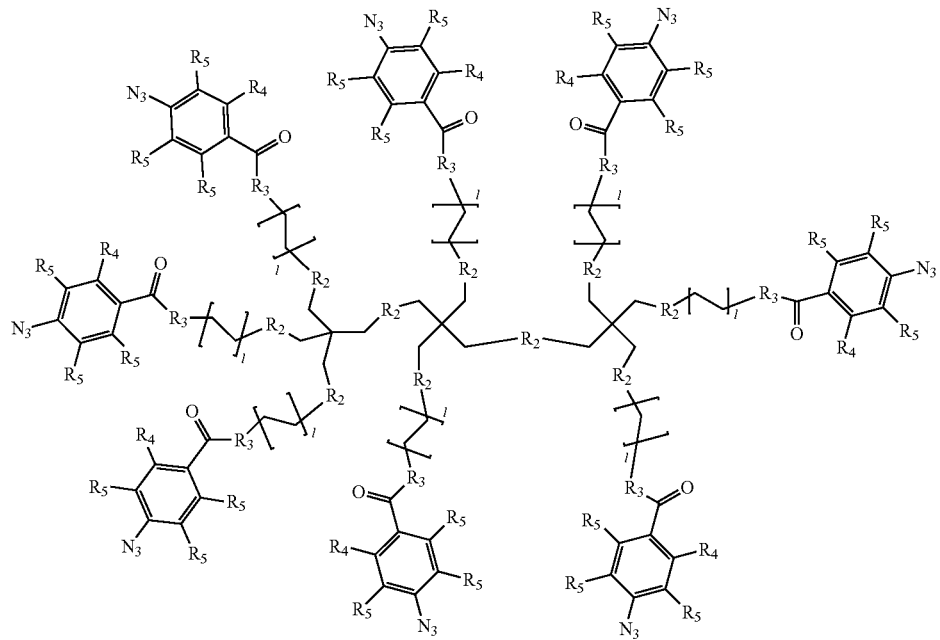

In Formula 2-1 to Formula 2-6, $R_2$ is O, S, NH, $CH_2$ or

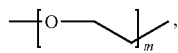

$R_3$ is O, S, NH or $CH_2$, $R_4$ is hydrogen, halogen, a linear type or branch type alkyl group of $C_1$ to $C_{30}$, a linear type or branch type alkoxy group of $C_1$ to $C_{30}$, a linear type or branch type alkyl group of $C_1$ to $C_{30}$, where at least one hydrogen is substituted with halogen, or a linear type or branch type alkoxy group of $C_1$ to $C_{30}$, where at least one hydrogen is substituted with halogen, $R_5$ is hydrogen or halogen, and "l" and "m" are each independently an integer of 1 to 30.

The compound represented by Formula 2 may include any one selected from Formula 3-1 to Formula 3-9 below.

[Formula 3-1]

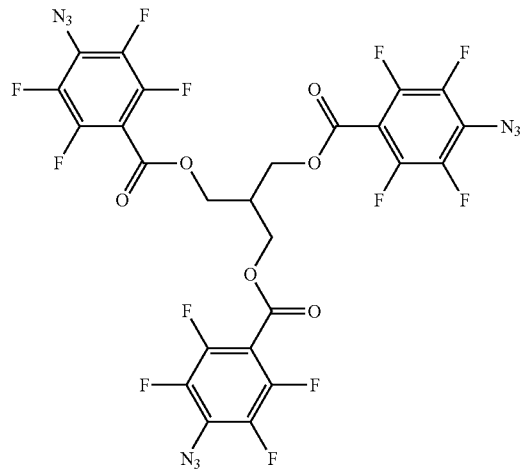

[Formula 3-2]

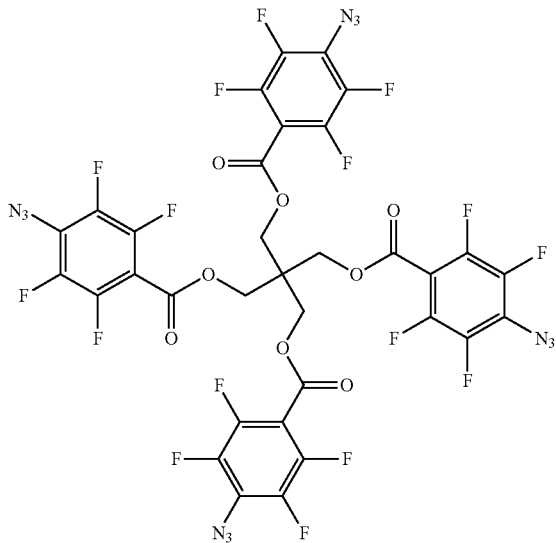

[Formula 3-3]
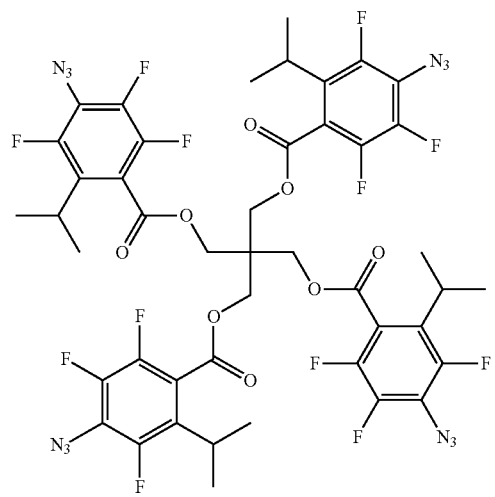
[Formula 3-4]
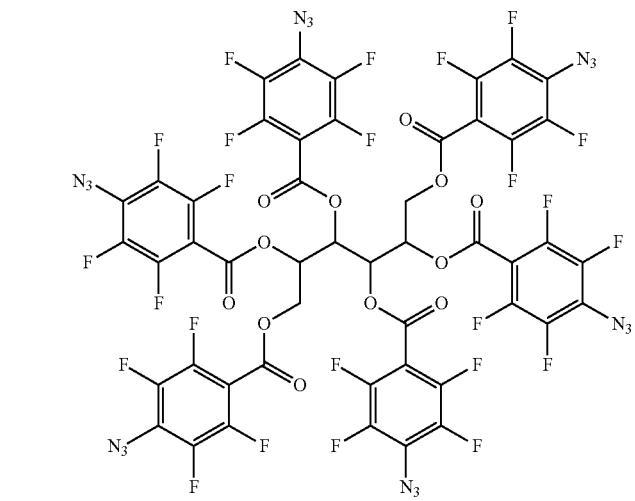
[Formula 3-5]
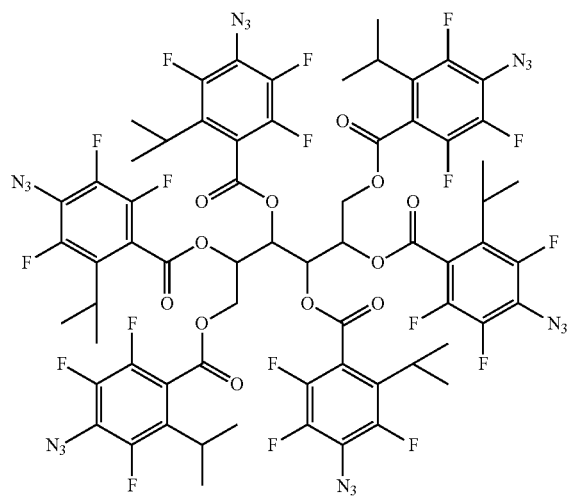
[Formula 3-6]
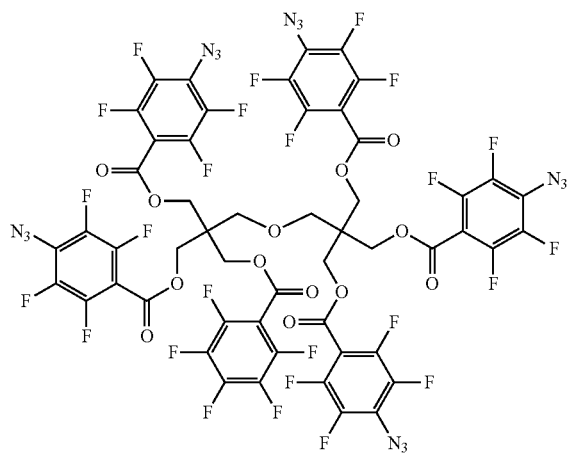
[Formula 3-7]
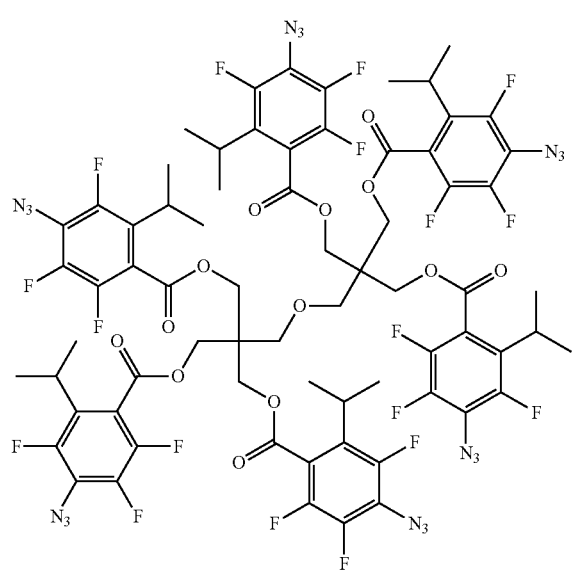

[Formula 3-8]

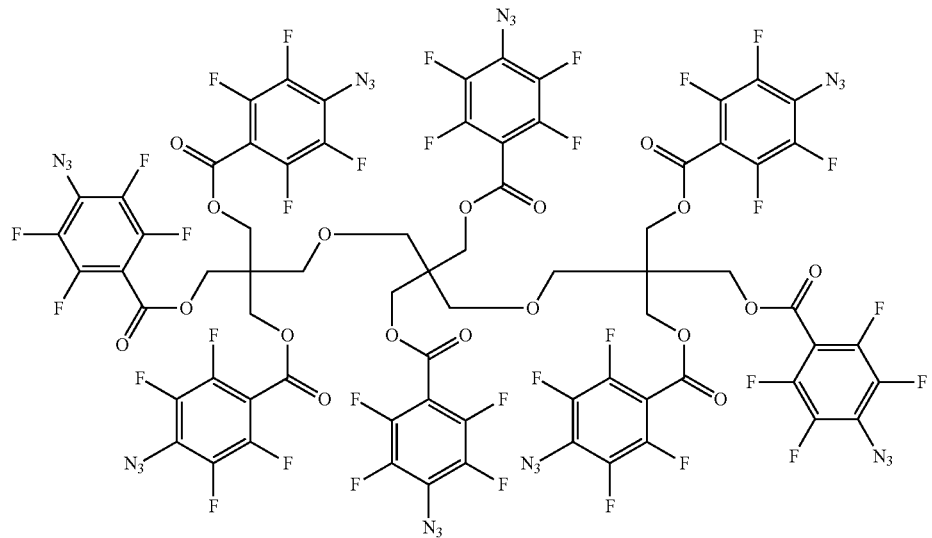

[Formula 3-9]

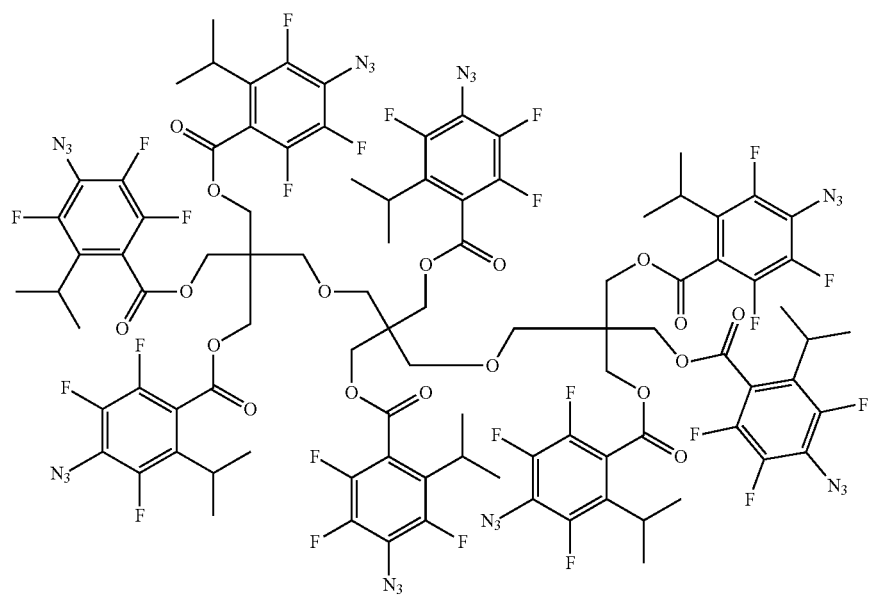

Referring to FIG. 2, a photomask 300 may be disposed on the lower layer 200. The photomask 300 may expose a portion of the lower mask 200. On the photomask 300, light 400 may be irradiated. By the light 400, the lower layer 200 may be exposed. The light 400 may be electron beam or extreme ultraviolet rays. On the first part 210 of the lower layer 200 exposed by the photomask 300, the light 400 may be directly irradiated. By the light 400, a crosslinker composition in the first part 210 of the lower layer 200 may be crosslinked and cured. Particularly, by the light 400, a portion of the chemical bonds of the crosslinker composition may be cleaved to form radicals. The radicals may be free radicals. For example, as shown below, $N_2$ is removed from the crosslinker composition represented by Formula 1, and N radicals (i.e., nitrene) may be formed. Due to the radicals, intermolecular bonding reaction between materials of Formula 1 may occur.

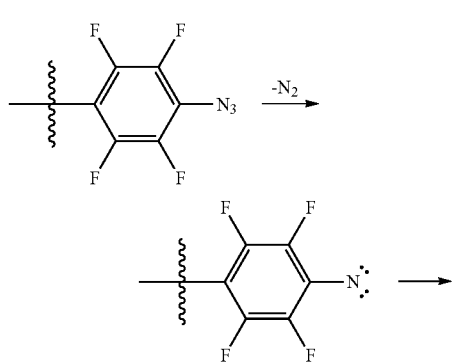

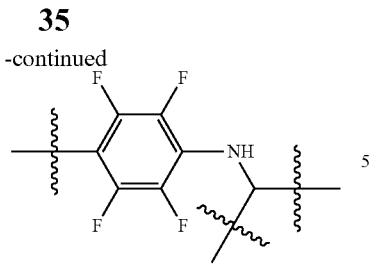

The second part 220 of the lower layer 200, unexposed by the photomask 300 may not be exposed to the light 400. That is, the crosslinker composition in the second part 220 of the lower layer 200 may be uncured.

Referring to FIG. 3, the photomask 300 may be removed. The second part 220 of the lower layer 200 may be removed using a solution, and the first part 210 of the lower layer 200 may remain to form a lower pattern. Hereinafter, the first part 210 of the lower layer 200 may be referred to as a lower pattern. The lower pattern may be the constituent element of an electronic device. For example, the lower pattern may be any one among an electrode layer, a charge transport layer, an active layer and an insulating layer constituting an electronic device. For example, the electronic device may be an organic thin film transistor, a logic electronic device, an organic light-emitting device (OLED), or a quantum dot light-emitting diode (QD-LED).

The three-dimensional crosslinker composition according to embodiments of the inventive concept may be used for forming a pattern or for manufacturing an electronic device. For example, the crosslinker composition may be used for a patterning process for manufacturing an electronic device. According to the inventive concept, a photoresist layer for forming a pattern or for manufacturing an electronic device may not be required. Accordingly, a manufacturing process may be simplified, and at the same time, the damage of the constituent elements of an electronic device may be prevented. Further, the electric properties and stability of an electronic device manufactured using a three-dimensional crosslinker composition may be improved.

Therefore, the generating phenomenon of contaminations due to a metal element in a manufacturing process of a semiconductor device may be prevented.

Hereinafter, a method of preparing the three-dimensional crosslinker composition according to embodiments of the inventive concept will be explained.

Example 1

Synthesis of 2-(((4-azido-2,3,5,6-tetrafluorobenzoyl) oxy)methyl)propane-1,3-diyl bis(4-azido-2,3,5,6-tetrafluorobenzoate) (3Bx)

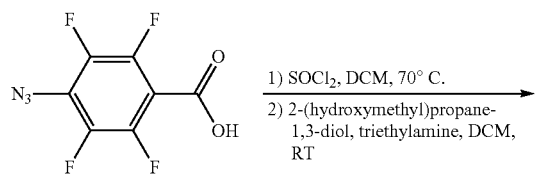

1) $SOCl_2$, DCM, 70° C.
2) 2-(hydroxymethyl)propane-1,3-diol, triethylamine, DCM, RT

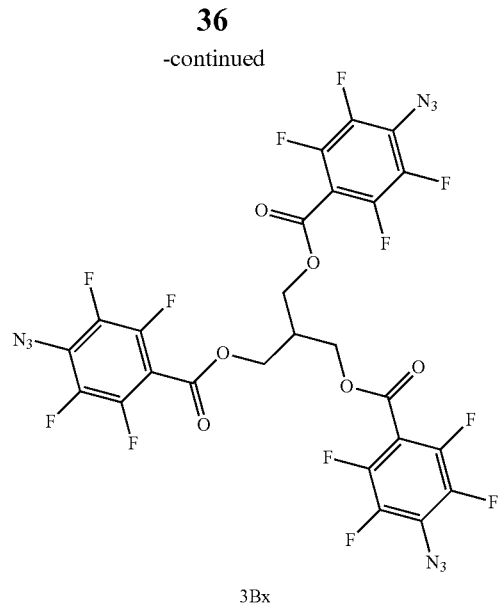

3Bx

To a 25 ml round-bottom flask, a magnetic bar was put and prepared. The round-bottom flask was vacuum dried while heating with a torch, and the flask was charged with argon. To the flask, 4-azido-2,3,5,6-tetrafluorobenzoic acid (0.30 g, 1.28 mmol) was added, and vacuum drying was performed while stirring at room temperature for about 2 hours. To the flask, thionyl chloride ($SOCl_2$) (0.21 mL, 2.84 mmol) and anhydrous dichloromethane (DCM) (6 mL) were added in order to prepare a mixture. The mixture was heated to about 70° C., and stirred at about 70° C. for about 26 hours. The mixture was cooled to room temperature (about 25° C.), organic solvents were removed by a rotary evaporator, and additional drying was performed using a vacuum pump to obtain a product. The product was diluted in anhydrous dichloromethane (6 mL) to prepare a first mixture, and the first mixture was prepared under an argon atmosphere.

To a separate 25 ml round-bottom flask, a magnetic bar was put and prepared. The round-bottom flask was vacuum dried while heating with a torch, and the flask was charged with argon. To the flask, 2-(hydroxymethyl)propane-1,3-diol (37.40 mg, 0.35 mmol) was added, and vacuum drying was performed while stirring at room temperature for about 2 hours. To the flask, anhydrous dichloromethane (8 mL) and triethylamine (0.18 mL, 1.27 mmol) were added in order to prepare a mixture. To the mixture, the first mixture prepared first was added dropwisely to prepare a second mixture. The second mixture was stirred at room temperature for about 22 hours, and distilled water (15 mL) was added to terminate the reaction. An extracting process of the second mixture was performed using an extraction funnel and dichloromethane (20 mL). The extracting process was repeated three times, moisture in the organic layer thus obtained was removed using anhydrous $MgSO_4$, and organic solvents were removed using a rotary evaporator. The organic material thus obtained was separated by silica gel column chromatography (ethyl acetate:n-hexane=3:1), and a pure white solid product was obtained by a recrystallization method using n-hexane. The solid product was 0.14 g, and the yield was analyzed as 52%.

Example 2

Synthesis of 2,2-bis(((4-azido-2,3,5,6-tetrafluorobenzoyl)oxy)methyl)propane-1,3-diyl bis(4-azido-2,3,5,6-tetrafluorobenzoate) (4Bx)

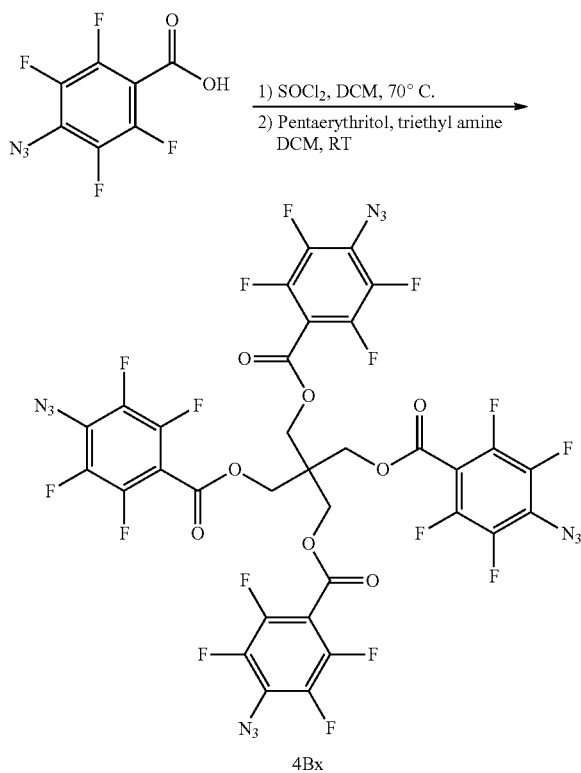 [SMILES: [N-]=[N+]=Nc1c(F)c(F)c(C(=O)O)c(F)c1F ; [N-]=[N+]=Nc1c(F)c(F)c(C(=O)OCC(COC(=O)c2c(F)c(F)c(N=[N+]=[N-])c(F)c2F)(COC(=O)c2c(F)c(F)c(N=[N+]=[N-])c(F)c2F)COC(=O)c2c(F)c(F)c(N=[N+]=[N-])c(F)c2F)c(F)c1F]

4Bx

To a 50 ml round-bottom flask, a magnetic bar was put and prepared. The round-bottom flask was vacuum dried while heating with a torch, and the flask was charged with argon. To the flask, 4-azido-2,3,5,6-tetrafluorobenzoic acid (1.00 g, 4.25 mmol) was added, and vacuum drying was performed while stirring at room temperature for about 2 hours. To the flask, thionyl chloride (0.62 mL, 8.50 mmol) and anhydrous dichloromethane (25 mL) were added in order to prepare a mixture. The mixture was heated to about 70° C., and stirred at about 70° C. for about 16 hours. The mixture was cooled to room temperature (about 25° C.), organic solvents were removed by a rotary evaporator, and additional drying was performed using a vacuum pump to obtain a product. The product was diluted in anhydrous dichloromethane (6 mL) to prepare a first mixture, and the first mixture was prepared under an argon atmosphere.

To a separate 50 ml round-bottom flask, a magnetic bar was put and prepared. The round-bottom flask was vacuum dried while heating with a torch, and the flask was charged with argon. To the flask, pentaerythritol (0.12 g, 0.88 mmol) was added, and vacuum drying was performed while stirring at room temperature for about 2 hours. To the flask, anhydrous dichloromethane (15 mL) and triethylamine (0.59 mL, 4.25 mmol) were added in order to prepare a mixture. To the mixture, the first mixture prepared first was added dropwisely to prepare a second mixture. The second mixture was stirred at room temperature for about 26 hours, and distilled water (10 mL) was added to terminate the reaction. An extracting process of the second mixture was performed using an extraction funnel, distilled water (20 mL) and dichloromethane (20 mL). The extracting process was repeated three times, moisture in the organic layer thus obtained was removed using anhydrous $MgSO_4$, and organic solvents were removed using a rotary evaporator. The organic material thus obtained was separated by silica gel column chromatography (ethyl acetate:n-hexane=3:1), and a pure white solid product was obtained by a recrystallization method using n-hexane. The solid product was 0.79 g, and the yield was analyzed as 89%.

Example 3

Synthesis of 2-4(4-azido-2,3,5,6-tetrafluorobenzoyl) oxy)methyl)-2-((3-((4-azido-2,3,5,6-tetrafluorobenzoyl)oxy)-2,2-bis(((4-azido-2,3,5,6-tetrafluorobenzoyl)oxy)methyl)propoxy)methyl)propane-1,3-diylbis(4-azido-2,3,5,6-tetrafluorobenzoate) (6Bx)

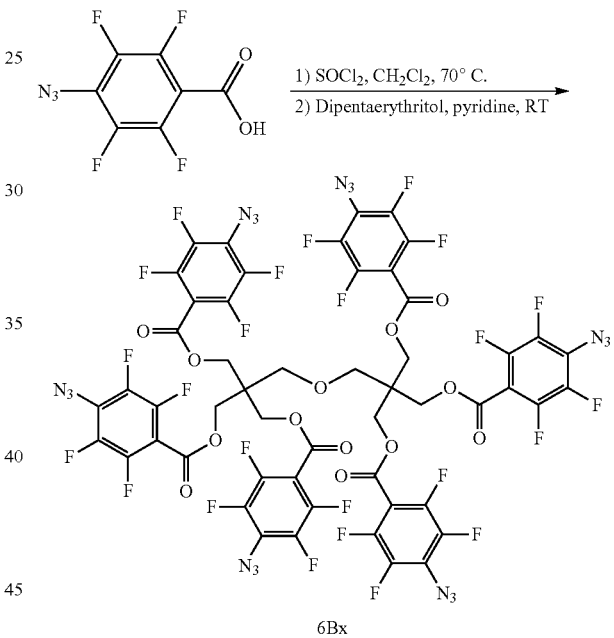

6Bx

To a 50 ml round-bottom flask, a magnetic bar was put and prepared. The round-bottom flask was vacuum dried while heating with a torch, and the flask was charged with argon. To the flask, 4-azido-2,3,5,6-tetrafluorobenzoic acid (1.50 g, 6.38 mmol) was added, and vacuum drying was performed while stirring at room temperature for about 2 hours. To the flask, thionyl chloride (0.66 mL, 9.12 mmol) and anhydrous dichloromethane (25 mL) were added in order to prepare a mixture. The mixture was heated to about 70° C., and stirred at about 70° C. for about 28 hours. The mixture was cooled to room temperature (about 25° C.), organic solvents were removed by a rotary evaporator, and additional drying was performed using a vacuum pump to obtain a product. The product was diluted in anhydrous dichloromethane (15 mL) to prepare a first mixture, and the first mixture was prepared under an argon atmosphere.

To a separate 50 ml round-bottom flask, a magnetic bar was put and prepared. The round-bottom flask was vacuum dried while heating with a torch, and the flask was charged with argon. To the flask, dipentaerythritol (0.19 g, 0.76 mmol) was added, and vacuum drying was performed while stirring at room temperature for about 2 hours. To the flask, anhydrous pyridine (25 mL) was added and stirred to prepare a mixture. To the mixture, the first mixture prepared first was added dropwisely to prepare a second mixture. The second mixture was stirred at room temperature for about 22 hours, and distilled water (15 mL) was added to terminate the reaction. An extracting process of the second mixture was performed using an extraction funnel, distilled water (35 mL) and dichloromethane (30 mL). The extracting process was repeated three times, moisture in the organic layer thus obtained was removed using anhydrous $MgSO_4$, and organic solvents were removed using a rotary evaporator. The organic material thus obtained was separated by silica gel column chromatography (dichloromethane:n-hexane=7:1), and a pure white solid product was obtained by a recrystallization method using n-hexane. The solid product was 0.86 g, and the yield was analyzed as 73%.

Example 4

Synthesis of hexane-1,2,3,4,5,6-hexayl hexakis(4-azido-2,3,5,6-tetrafluorobenzoate) (6Bx_M)

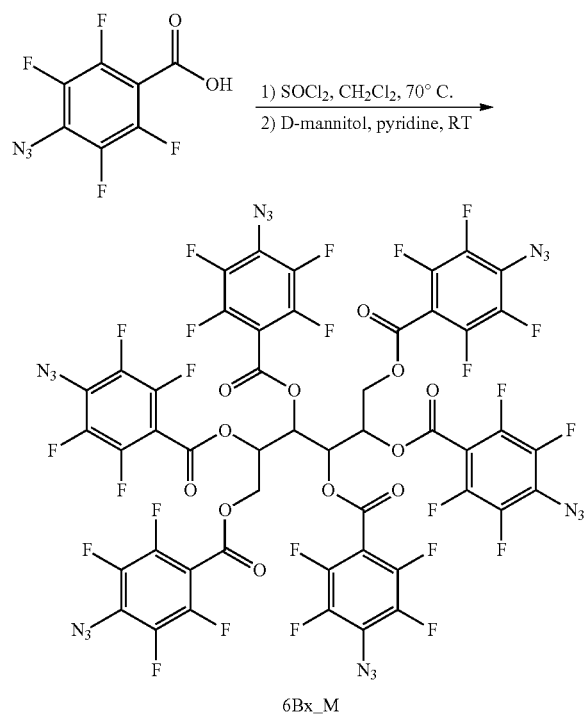

To a 50 ml round-bottom flask, a magnetic bar was put and prepared. The round-bottom flask was vacuum dried while heating with a torch, and the flask was charged with argon. To the flask, 4-azido-2,3,5,6-tetrafluorobenzoic acid (1.00 g, 4.25 mmol) was added, and vacuum drying was performed while stirring at room temperature for about 2 hours. To the flask, thionyl chloride (0.49 mL, 6.8 mmol) and anhydrous dichloromethane (20 mL) were added in order to prepare a mixture. The mixture was heated to about 70° C., and stirred at about 70° C. for about 23 hours. The mixture was cooled to room temperature (about 25° C.), organic solvents were removed by a rotary evaporator, and additional drying was performed using a vacuum pump to obtain a product. The product was diluted in anhydrous dichloromethane (12 mL) to prepare a first mixture, and the first mixture was prepared under an argon atmosphere.

To a separate 50 ml round-bottom flask, a magnetic bar was put and prepared. The round-bottom flask was vacuum dried while heating with a torch, and the flask was charged with argon. To the flask, D-mannitol (0.86 g, 0.47 mmol) was added, and vacuum drying was performed while stirring at room temperature for about 2 hours. To the flask, anhydrous pyridine (15 mL) was added and stirred to prepare a mixture. To the mixture, the first mixture prepared first was added dropwisely to prepare a second mixture. The second mixture was stirred at room temperature for about 22 hours, and distilled water (15 mL) was added to terminate the reaction. An extracting process of the second mixture was performed using an extraction funnel, distilled water (30 mL) and dichloromethane (25 mL). The extracting process was repeated three times, moisture in the organic layer thus obtained was removed using anhydrous $MgSO_4$, and organic solvents were removed using a rotary evaporator. The organic material thus obtained was separated by silica gel column chromatography (dichloromethane:n-hexane=7:1), and a pure white solid product was obtained by a recrystallization method using n-hexane. The solid product was 0.50 g, and the yield was analyzed as 71%.

Example 5

Synthesis of 2-((3-((4-azido-2,3,5,6-tetrafluorobenzoyl)oxy)-2,2-bis(((4-azido-2,3,5,6-tetrafluorobenzoyl)oxy)methyl)propoxy)methyl)-2-((3-((4-azido-2,3,5,6-tetrafluorobenzoyl)oxy)-2,2-bis(((4-azido-2,3,5,6-tetrafluorobenzoyl)oxy)methyl)propoxy)methyl)propane-1,3-diyl bis(4-azido-2,3,5,6-tetrafluorobenzoate) (8Bx)

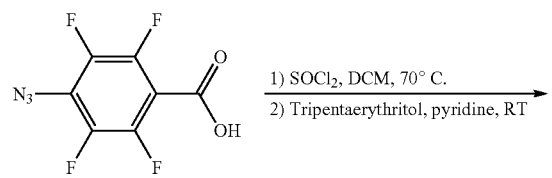

-continued

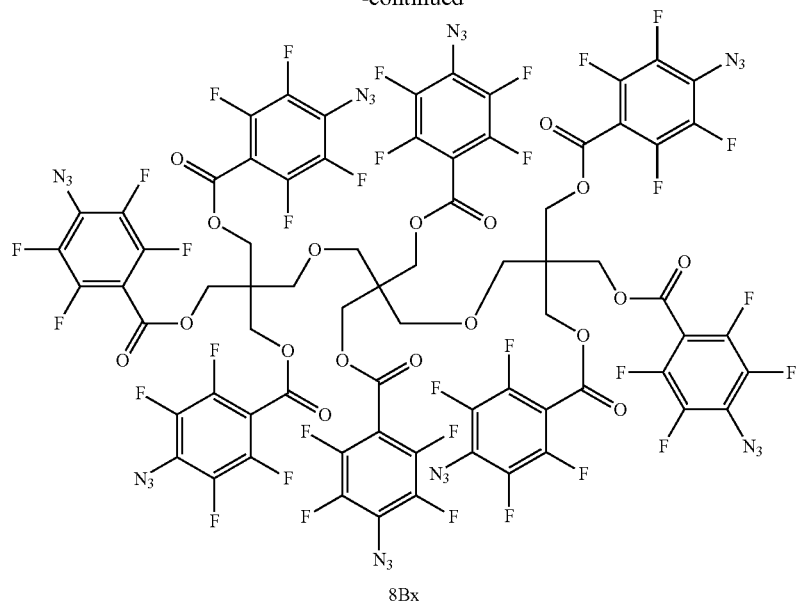

8Bx

To a 50 ml round-bottom flask, a magnetic bar was put and prepared. The round-bottom flask was vacuum dried while heating with a torch, and the flask was charged with argon. To the flask, 4-azido-2,3,5,6-tetrafluorobenzoic acid (2.00 g, 8.51 mmol) was added, and vacuum drying was performed while stirring at room temperature for about 2 hours. To the flask, thionyl chloride (0.99 mL, 13.62 mmol) and anhydrous dichloromethane (28 mL) were added in order to prepare a mixture. The mixture was heated to about 70° C., and stirred at about 70° C. for about 17 hours. The mixture was cooled to room temperature (about 25° C.), organic solvents were removed by a rotary evaporator, and additional drying was performed using a vacuum pump to obtain a product. The product was diluted in anhydrous dichloromethane (18 mL) to prepare a first mixture, and the first mixture was prepared under an argon atmosphere.

To a separate 100 ml round-bottom flask, a magnetic bar was put and prepared. The round-bottom flask was vacuum dried while heating with a torch, and the flask was charged with argon. To the flask, tripentaerythritol (0.26 g, 0.71 mmol) was added, and vacuum drying was performed while stirring at room temperature for about 2 hours. To the flask, anhydrous pyridine (38 mL) was added and stirred to prepare a mixture. To the mixture, the first mixture prepared first was added dropwisely to prepare a second mixture. The second mixture was stirred at room temperature for about 17 hours, and distilled water (18 mL) was added to terminate the reaction. An extracting process of the second mixture was performed using an extraction funnel, distilled water (40 mL) and dichloromethane (35 mL). The extracting process was repeated three times, moisture in the organic layer thus obtained was removed using anhydrous MgSO$_4$, and organic solvents were removed using a rotary evaporator. The organic material thus obtained was separated by silica gel column chromatography (dichloromethane:n-hexane=7:1), and a pure white solid product was obtained by a recrystallization method using n-hexane. The solid product was 0.40 g, and the yield was analyzed as 26%.

Example 6

Synthesis of 4-(4-azido-2,3,5-trifluoro-6-isopropylphenyl)-4-oxobutyl4-azido-2,3,5-trifluoro-6-isopropylbenzoate (IP-2Bx)

Example 6-1: Synthesis of 1,2,3,4-tetrafluoro-5-isopropylbenzene

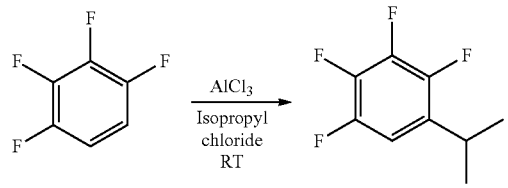

To a 50 ml round-bottom flask, a magnetic bar was put and prepared. The round-bottom flask was vacuum dried while heating with a torch, and the flask was charged with argon. To the flask, 1,2,3,4-tetrafluorobenzene (1.47 g, 9.60 mmol) and AlCl$_3$ (0.38 g, 2.89 mmol) were added and stirred under 0° C. conditions for about 30 minutes under an argon atmosphere. To the flask, isopropyl chloride (1.14 mL, 12.48 mmol) was added dropwisely. After about 1 hour, the temperature was raised to room temperature, and stirring was performed at room temperature for about 3 hours to prepare a mixture. The reaction of the mixture was terminated using distilled water, and an extracting process was performed using an extraction funnel and chloroform three times. Moisture in the organic layer obtained by the extracting process was removed using anhydrous MgSO$_4$, and organic solvents were removed using a rotary evaporator. The organic material thus obtained was filtered using silica gel and dichloromethane and dried through a rotary evaporator to obtain a turbid yellow oil state product. The product was 1.40 g, and the yield was analyzed as 76%.

Example 6-2: Synthesis of 2,3,4,5-tetrafluoro-6-isopropylbenzoic Acid

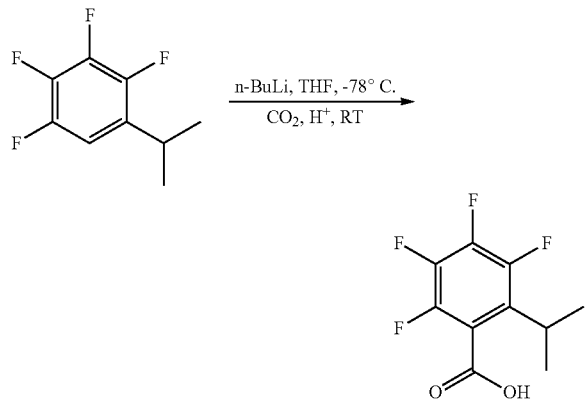

To a 250 ml round-bottom flask, a magnetic bar was put and prepared. The round-bottom flask was vacuum dried while heating with a torch, and the flask was charged with argon. To the flask, 1,2,3,4-tetrafluoro-5-isopropylbenzene (10.87 g, 56.58 mmol) and THF (110 mL) were added and stirred at about −78° C. for about 30 minutes under an argon atmosphere. To the flask, n-BuLi (42.4 mL, 67.90 mmol) was added dropwisely. After about 2 hours, a carbon dioxide gas was bubbled at about −78° C. for about 30 minutes. Then, stirring was performed for about 14 hours while slowly raising the temperature to room temperature. Under 0° C. conditions, 80 mL of 1 M HCl was added to the flask dropwisely to prepare a mixture. An extracting process of the mixture was performed using an extraction funnel, 100 mL of distilled water and ethyl acetate, three times. Moisture in the organic layer obtained by the extracting process was removed using anhydrous $MgSO_4$, and organic solvents were removed using a rotary evaporator. The organic material thus obtained was dried using a vacuum pump to obtain a white solid product. The solid product was 8.28 g, and the yield was analyzed as 62%.

Example 6-3: Synthesis of ethane-1,2-diyl bis(2,3,4,5-tetrafluoro-6-isopropylbenzoate)

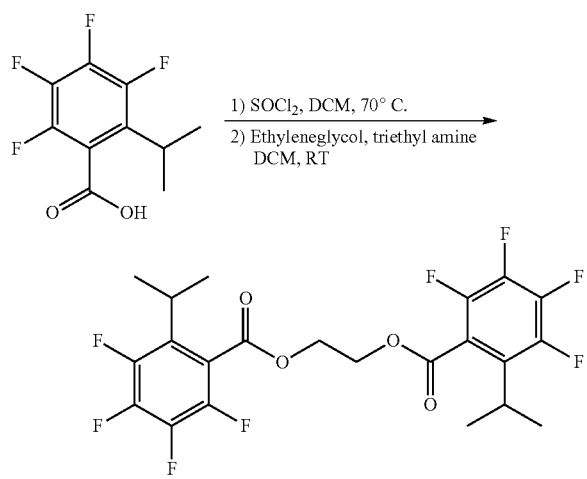

To a 25 ml round-bottom flask, a magnetic bar was put and prepared. The round-bottom flask was vacuum dried while heating with a torch, and the flask was charged with argon. To the flask, 2,3,4,5-tetrafluoro-6-isopropylbenzoic acid (0.5 g, 2.12 mmol) was added, and vacuum drying was performed while stirring at room temperature for about 2 hours. To the flask, thionyl chloride (0.61 mL, 8.49 mmol) and anhydrous dichloromethane (10 mL) were added in order to prepare a mixture. The mixture was heated to about 70° C., and stirred at about 70° C. for about 18 hours. The mixture was cooled to room temperature, organic solvents were removed by a rotary evaporator, and additional drying was performed using a vacuum pump to obtain a product. The product was diluted in anhydrous dichloromethane (8 mL) to prepare a first mixture, and the first mixture was prepared under an argon atmosphere.

To a separate 25 ml round-bottom flask, a magnetic bar was put and prepared. The round-bottom flask was vacuum dried while heating with a torch, and the flask was charged with argon. To the flask, ethylene glycol (0.053 g, 0.85 mmol), trimethylamine (0.6 mL, 4.23 mmol) and anhydrous dichloromethane (8 mL) were added to prepare a mixture. To the mixture, the first mixture prepared first was added dropwisely to prepare a second mixture. The second mixture was stirred at room temperature for about 26 hours, and distilled water (6 mL) was added to terminate the reaction. An extracting process of the second mixture was performed using an extraction funnel, distilled water (15 mL) and dichloromethane (25 mL). The extracting process was repeated three times, moisture in the organic layer thus obtained was removed using anhydrous $MgSO_4$, and organic solvents were removed using a rotary evaporator. The organic material thus obtained was separated by silica gel column chromatography (ethyl acetate:n-hexane=1:10) to obtain a white solid product. The solid product was 0.342 g, and the yield was analyzed as 81%.

Example 6-4: Synthesis of 4-(4-azido-2,3,5-trifluoro-6-isopropylphenyl)-4-oxobutyl4-azido-2,3,5-trifluoro-6-isopropylbenzoate (IP-2Bx)

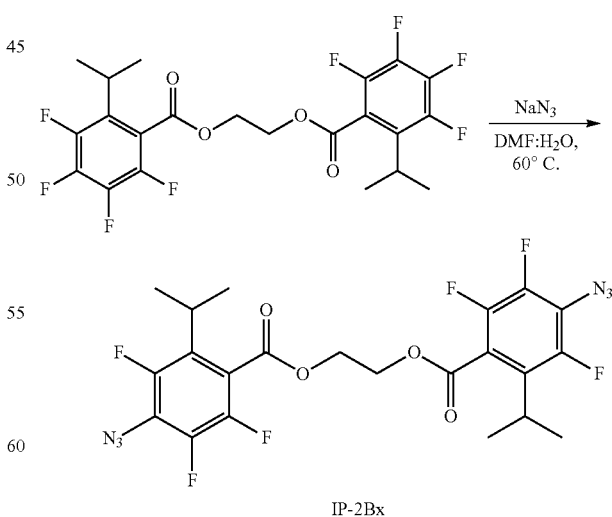

A 10 mL brown vial containing an oven-dried magnetic bar was prepared. To the vial, ethane-1,2-diyl bis(2,3,4,5-tetrafluoro-6-isopropylbenzoate) (0.34 g, 0.68 mmol) and sodium azide (0.13 g, 2.05 mmol) were added, and distilled water (0.7 mL) and DMF (7 mL) were added thereto, followed by stirring on a hot plate of about 60° C. for about 19 hours. After cooling the vial to room temperature, an extracting process was performed using an extraction funnel, 25 mL of distilled water, ethyl acetate (8 mL) and n-hexane (2 mL), four times. Moisture in the organic layer thus obtained was removed using anhydrous $MgSO_4$, and organic solvents were removed using a rotary evaporator. The organic material thus obtained was separated by silica gel column chromatography (chloroform:n-hexane=1:2) to obtain a white solid final product. The solid product was 0.35 g, and the yield was analyzed as 94%.

Example 7

Synthesis of 2,2-bis(((4-azido-2,3,5-trifluoro-6-isopropylbenzoyl)oxy)methyl)propane-1,3-diyl bis(4-azido-2,3,5-trifluoro-6-isopropylbenzoate) (IP-4Bx)

Example 7-1: Synthesis of 2,2-bis(((2,3,4,5-tetrafluoro-6-isopropylbenzoyl)oxy)methyl)propane-1,3-diyl bis(2,3,4,5-tetrafluoro-6-isopropylbenzoate)

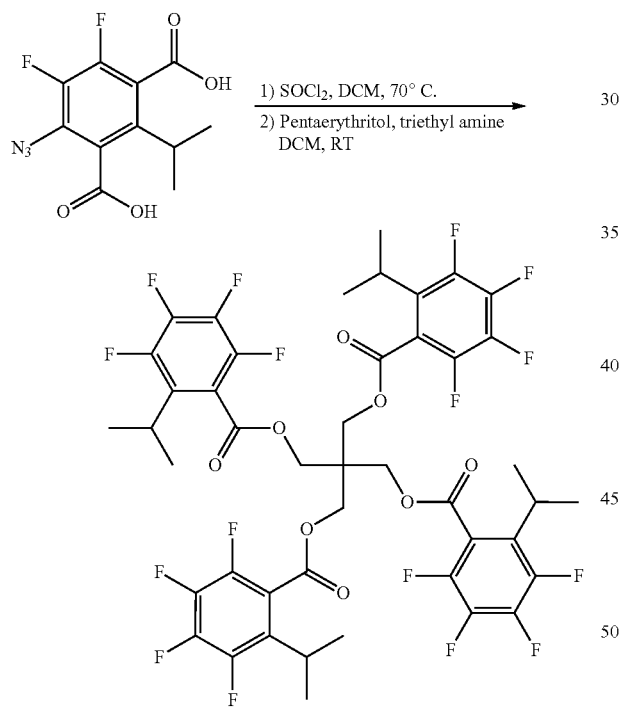

To a 25 ml round-bottom flask, a magnetic bar was put and prepared. The round-bottom flask was vacuum dried while heating with a torch, and the flask was charged with argon. To the flask, 2,3,4,5-tetrafluoro-6-isopropylbenzoic acid (1.0 g, 4.23 mmol) was added, and vacuum drying was performed while stirring at room temperature for about 2 hours. To the flask, thionyl chloride (2 mL, 27.57 mmol) and anhydrous dichloromethane (10 mL) were added in order, heated to about 70° C., and stirred at about 70° C. for about 22 hours to prepare a mixture. The mixture was cooled to room temperature, organic solvents were removed by a rotary evaporator, and additional drying was performed using a vacuum pump to obtain a product. The product was diluted in anhydrous dichloromethane (10 mL) to prepare a first mixture, and the first mixture was prepared under an argon atmosphere.

To a separate 50 ml round-bottom flask, a magnetic bar was put and prepared. The round-bottom flask was vacuum dried while heating with a torch, and the flask was charged with argon. To the flask, pentaerythritol (0.11 g, 0.81 mmol) and anhydrous pyridine (10 mL) were added and stirred to prepare a mixture. To the mixture, the first mixture prepared first was added dropwisely to prepare a second mixture. The second mixture was stirred at room temperature for about 34 hours, and distilled water (10 mL) was added to terminate the reaction. An extracting process was performed using an extraction funnel, distilled water (20 mL) and dichloromethane (35 mL). The extracting process was repeated three times, moisture in the organic layer thus obtained was removed using anhydrous $MgSO_4$, and organic solvents were removed using a rotary evaporator. The organic material thus obtained was separated by silica gel column chromatography (ethyl acetate:n-hexane=1:8) to obtain a white solid product. The solid product was 0.51 g, and the yield was analyzed as 61.7%.

Example 7-2: Synthesis of 2,2-bis(((4-azido-2,3,5-trifluoro-6-isopropylbenzoyl)oxy)methyl)propane-1,3-diyl bis(4-azido-2,3,5-trifluoro-6-isopropylbenzoate) (IP-4Bx)

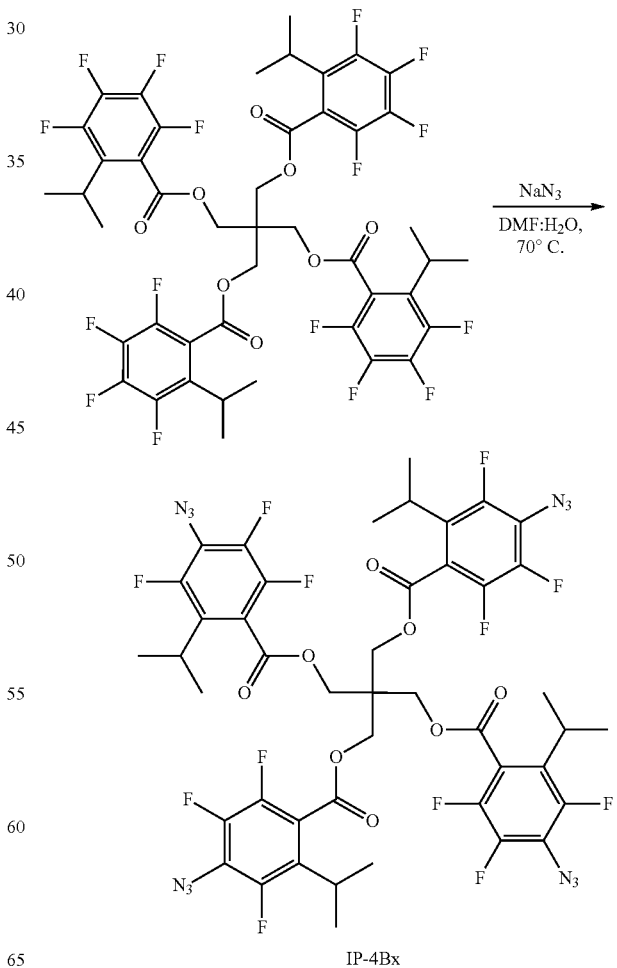

A 10 mL brown vial containing an oven-dried magnetic bar was prepared. To the vial, 2,2-bis(((2,3,4,5-tetrafluoro-6-isopropylbenzoyl)oxy)methyl)propane-1,3-diyl bis(2,3,4,5-tetrafluoro-6-isopropylbenzoate) (0.40 g, 0.40 mmol), sodium azide (0.26 g, 4.00 mmol), distilled water (0.4 mL) and DMF (3.6 mL) were added, followed by stirring on a hot plate of about 70° C. for about 39 hours to prepare a mixture. After cooling the mixture to room temperature, an extracting process was performed using an extraction funnel, distilled water (30 mL), ethyl acetate (20 mL) and n-hexane (4 mL), four times. Moisture in the organic layer thus obtained was removed using anhydrous MgSO$_4$, and organic solvents were removed using a rotary evaporator. The organic material thus obtained was separated by silica gel column chromatography (chloroform:n-hexane=1:2) to obtain a white solid final product. The solid product was 0.42 g, and the yield was analyzed as 95.6%.

Example 8

Synthesis of 2-4(4-azido-2,3,5,6-tetrafluorobenzoyl)oxy)methyl)-2-((3-((4-azido-2,3,5,6-tetrafluorobenzoyl)oxy)-2,2-bis(((4-azido-2,3,5,6-tetrafluorobenzoyl)oxy)methyl)propoxy)methyl)propane-1,3-diylbis(4-azido-2,3,5-trifluoro-6-isopropylbenzoate) (IP-6Bx)

Example 8-1: Synthesis of 2-(((2,3,4,5-tetrafluoro-6-isopropylbenzoyl)oxy)methyl)-2-((3-((4-azido-2,3,5,6-tetrafluorobenzoyl)oxy)-2,2-bis(((4-azido-2,3,5,6-tetrafluorobenzoyl)oxy)methyl)propoxy)methyl)propane-1,3-diylbis(2,3,4,5-tetrafluoro-6-isopropylbenzoate)

To a 25 ml round-bottom flask, a magnetic bar was put and prepared. The round-bottom flask was vacuum dried while heating with a torch, and the flask was charged with argon. To the flask, 2,3,4,5-tetrafluoro-6-isopropylbenzoic acid (1.0 g, 4.23 mmol) was added, and vacuum drying was performed while stirring at room temperature for about 2 hours. To the flask, thionyl chloride (2 mL, 27.57 mmol) and anhydrous dichloromethane (10 mL) were added in order to prepare a mixture. The mixture was heated to about 70° C., and stirred at about 70° C. for about 17 hours. The mixture was cooled to room temperature, organic solvents were removed by a rotary evaporator, and additional drying was performed using a vacuum pump to obtain a product. The product was diluted in anhydrous dichloromethane (10 mL) to prepare a first mixture, and the first mixture was prepared under an argon atmosphere.

To a separate 50 ml round-bottom flask, a magnetic bar was put and prepared. The round-bottom flask was vacuum dried while heating with a torch, and the flask was charged with argon. To the flask, dipentaerythritol (0.16 g, 0.55 mmol) and anhydrous pyridine (10 mL) were added and stirred to prepare a mixture. To the mixture, the first mixture prepared first was added dropwisely to prepare a second mixture. The second mixture was stirred at room temperature for about 29 hours, and distilled water (8 mL) was added to terminate the reaction. An extracting process was performed using an extraction funnel, distilled water (20 mL) and dichloromethane (30 mL). The extracting process was repeated three times, moisture in the organic layer thus obtained was removed using anhydrous MgSO$_4$, and organic solvents were removed using a rotary evaporator. The organic material thus obtained was separated by silica gel column chromatography (ethyl acetate:n-hexane=1:7) to obtain a white solid product. The solid product was 0.40 g, and the yield was analyzed as 46.3%.

Example 8-2: Synthesis of 2-(((4-azido-2,3,5,6-tetrafluorobenzoyl)oxy)methyl)-2-((3-((4-azido-2,3,5,6-tetrafluorobenzoyl)oxy)-2,2-bis(((4-azido-2,3,5,6-tetrafluorobenzoyl)oxy)methyl)propoxy)methyl)propane-1,3-diylbis(4-azido-2,3,5-trifluoro-6-isopropylbenzoate) (IP-6Bx)

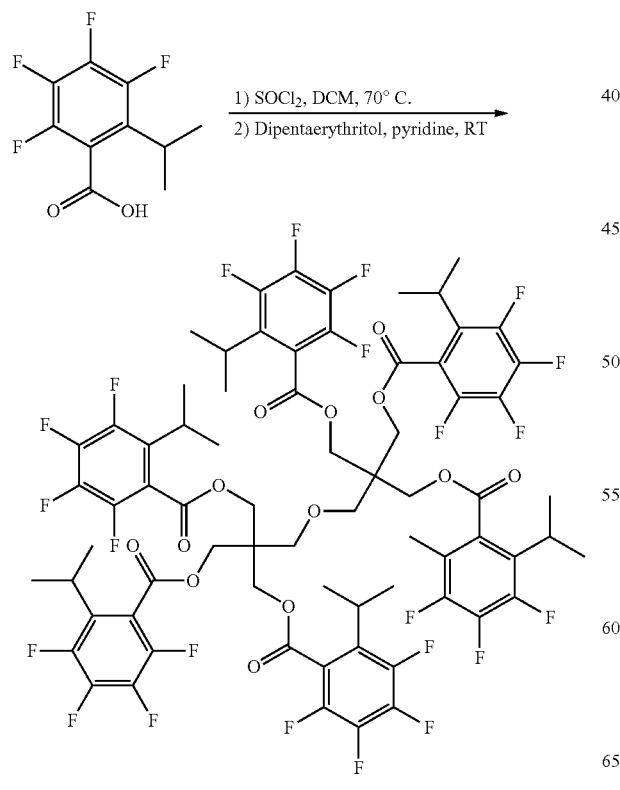

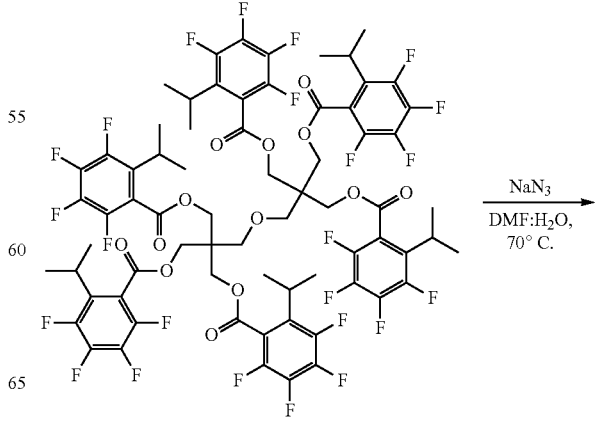

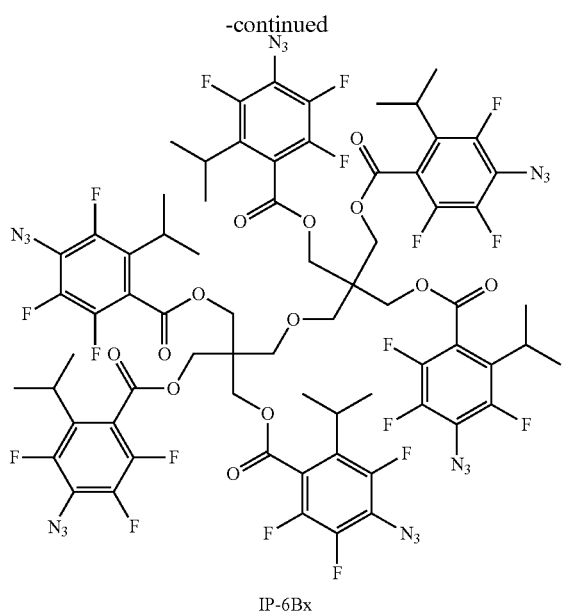

IP-6Bx

A 20 mL brown vial containing an oven-dried magnetic bar was prepared. To the vial, 2,2-bis(((2,3,4,5-tetrafluoro-6-isopropylbenzoyl)oxy)methyl)propane-1,3-diyl bis(2,3,4,5-tetrafluoro-6-isopropylbenzoate) (0.36 g, 0.40 mmol), sodium azide (0.13 g, 2.06 mmol), distilled water (1.0 mL) and DMF (10 mL) were added, followed by stirring on a hot plate of about 70° C. for about 19 hours. After cooling the mixture to room temperature, an extracting process was performed using an extraction funnel, 15 mL of distilled water, ethyl acetate (15 mL) and n-hexane (3 mL), four times. Moisture in the organic layer thus obtained was removed using anhydrous MgSO₄, and organic solvents were removed using a rotary evaporator. The organic material thus obtained was separated by silica gel column chromatography (chloroform:n-hexane=1:1) to obtain a white solid final product. The solid product was 0.36 g, and the yield was analyzed as 91.9%.

Example 9

Synthesis of 2-((3-(3-((4-azido-2,3,5-fluoro-6-isopropylbenzoyl)oxy)-2,2-bis(((4-azido-2,3,5-fluoro-6-isopropylbenzoyl)oxy)methyl)propoxy)-2,2-bis(((4-azido-2,3,5-fluoro-6-isopropylbenzoyl)oxy)methyl)propoxy)methyl)-2-(((4-azido-2,3,5-trifluoro-6-isopropylbenzoyl)oxy)methyl)propane-1,3-diyl bis(4-azido-2,3,5-trifluoro-6-isopropylbenzoate)) (IP-8Bx)

Example 9-1: Synthesis of 2-((3-(3-((2,3,4,5-tetrafluoro-6-isopropylbenzoyl)oxy)-2,2-bis(((2,3,4,5-tetrafluoro-6-isopropylbenzoyl)oxy)methyl)propoxy)-2,2-bis(((2,3,4,5-tetrafluoro-6-isopropylbenzoyl)oxy)methyl)propoxy)methyl)-2-(((2,3,4,5-tetrafluoro-6-isopropylbenzoyl)oxy)methyl)propane-1,3-diyl bis(2,3,4,5-tetrafluoro-6-isopropylbenzoate)

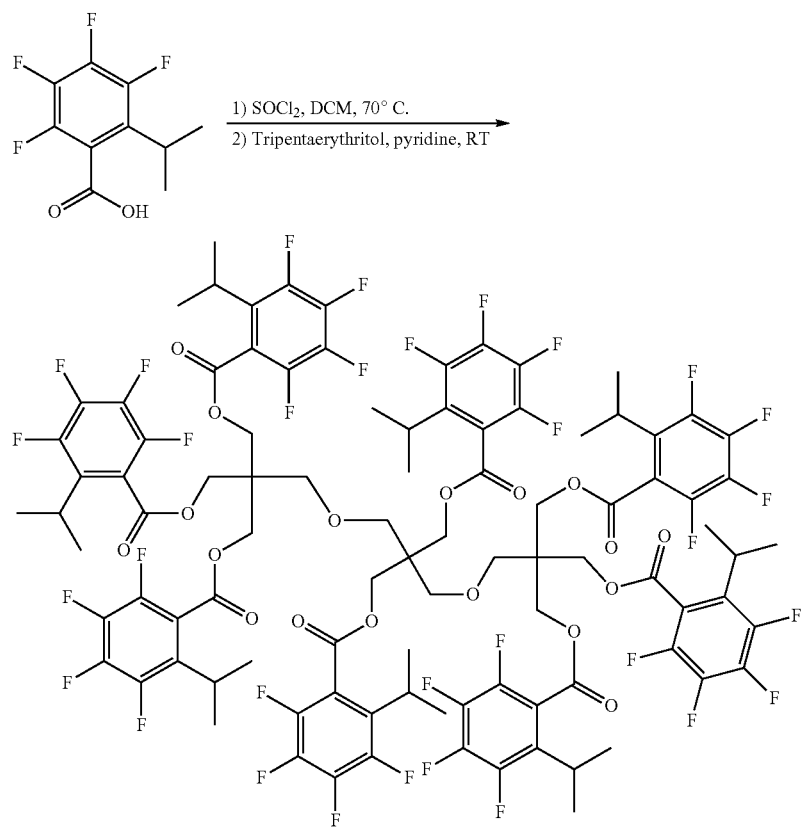 [SMILES: CC(C)c1c(F)c(F)c(F)c(F)c1C(=O)O ; CC(C)c1c(F)c(F)c(F)c(F)c1C(=O)OCC(COCC(COC(=O)c1c(F)c(F)c(F)c(F)c1C(C)C)(COC(=O)c1c(F)c(F)c(F)c(F)c1C(C)C)COC(=O)c1c(F)c(F)c(F)c(F)c1C(C)C)(COCC(COC(=O)c1c(F)c(F)c(F)c(F)c1C(C)C)(COC(=O)c1c(F)c(F)c(F)c(F)c1C(C)C)COC(=O)c1c(F)c(F)c(F)c(F)c1C(C)C)COC(=O)c1c(F)c(F)c(F)c(F)c1C(C)C]

To a 25 ml round-bottom flask, a magnetic bar was put and prepared. The round-bottom flask was vacuum dried while heating with a torch, and the flask was charged with argon. To the flask, 2,3,4,5-tetrafluoro-6-isopropylbenzoic acid (1.98 g, 8.40 mmol) was added, and vacuum drying was performed while stirring at room temperature for about 2 hours. To the flask, thionyl chloride (3.04 mL, 42 mmol) and anhydrous dichloromethane (15 mL) were added in order to prepare a mixture. The mixture was heated to about 70° C., and stirred at about 70° C. for about 16 hours. The mixture was cooled to room temperature, organic solvents were removed by a rotary evaporator, and additional drying was performed using a vacuum pump to obtain a product. The product was diluted in anhydrous dichloromethane (15 mL) to prepare a first mixture, and the first mixture was prepared under an argon atmosphere.

To a separate 50 ml round-bottom flask, a magnetic bar was put and prepared. The round-bottom flask was vacuum dried while heating with a torch, and the flask was charged with argon. To the flask, tripentaerythritol (0.26 g, 0.52 mmol) and anhydrous pyridine (14 mL) were added and stirred to prepare a mixture. To the mixture, the first mixture prepared first was added dropwisely to prepare a second mixture. The second mixture was stirred at room temperature for about 34 hours, and distilled water (10 mL) was added to terminate the reaction. An extracting process was performed using an extraction funnel, distilled water (25 mL) and dichloromethane (35 mL). The extracting process was repeated three times, moisture in the organic layer thus obtained was removed using anhydrous MgSO₄, and organic solvents were removed using a rotary evaporator. The organic material thus obtained was separated by silica gel column chromatography (ethyl acetate:n-hexane=1:7) to obtain a white solid product. The solid product was 0.35 g, and the yield was analyzed as 32%.

Example 9-2: 2-((3-(3-((4-azido-2,3,5-fluoro-6-isopropylbenzoyl)oxy)-2,2-bis(((4-azido-2,3,5-fluoro-6-isopropylbenzoyl)oxy)methyl)propoxy)-2,2-bis(((4-azido-2,3,5-fluoro-6-isopropylbenzoyl)oxy)methyl)propoxy)methyl)-2-(((4-azido-2,3,5-trifluoro-6-isopropylbenzoyl)oxy)methyl)propane-1,3-diyl bis (4-azido-2,3,5-trifluoro-6-isopropylbenzoate)) (IP-8Bx)

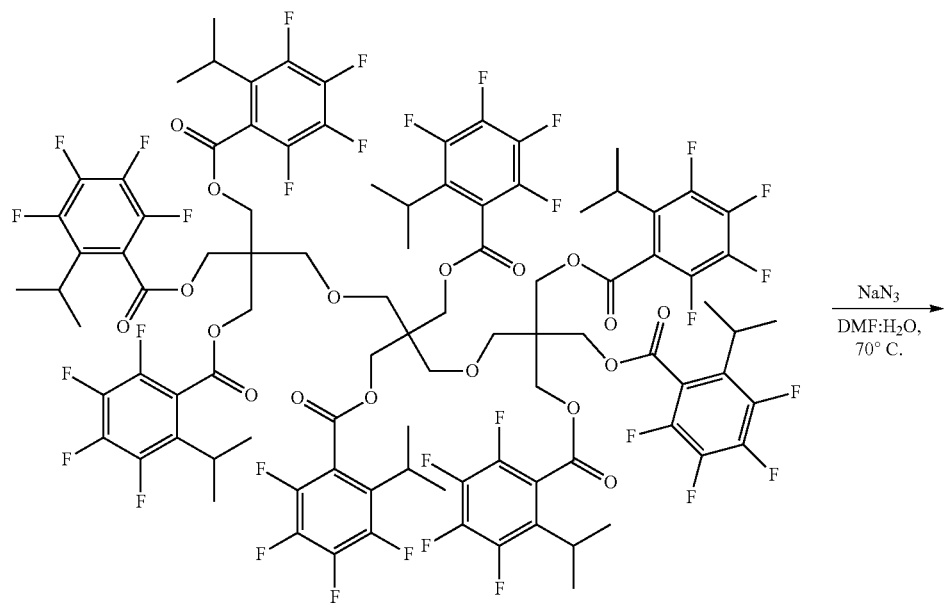

-continued

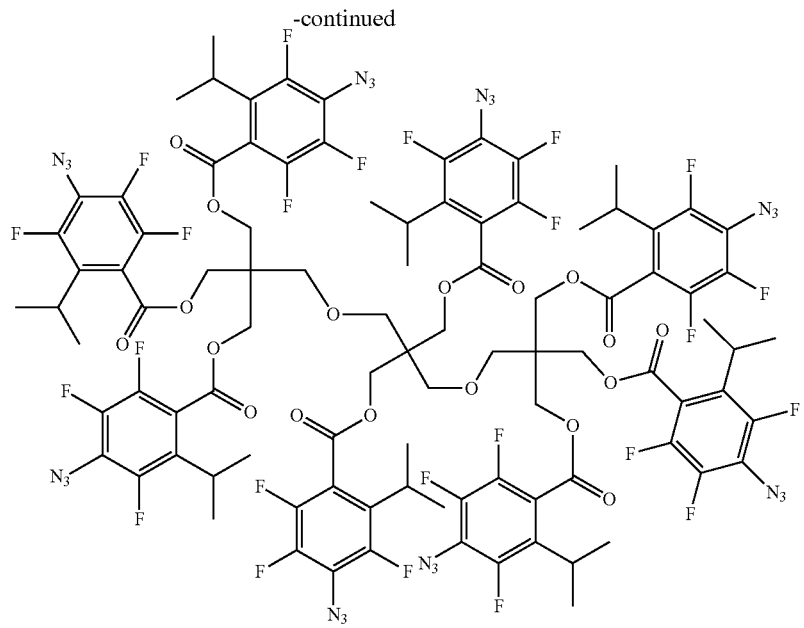

A 20 mL brown vial containing an oven-dried magnetic bar was prepared. To the vial, 2-((3-(3-(((2,3,4,5-tetrafluoro-6-isopropylbenzoyl)oxy)-2,2-bis(((2,3,4,5-tetrafluoro-6-isopropylbenzoyl)oxy)methyl)propoxy)-2,2-bis(((2,3,4,5-tetrafluoro-6-isopropylbenzoyl)oxy)methyl)propoxy)methyl)-2-(((2,3,4,5-tetrafluoro-6-isopropylbenzoyl)oxy)methyl) propane-1,3-diyl bis(2,3,4,5-tetrafluoro-6-isopropylbenzoate) (0.30 g, 0.14 mmol), sodium azide (0.14 g, 2.24 mmol), distilled water (1.0 mL) and DMF (15 mL) were added, followed by stirring on a hot plate of about 70° C. for about 26 hours. After cooling the mixture to room temperature, an extracting process was performed using an extraction funnel, 15 mL of distilled water, ethyl acetate (15 mL) and n-hexane (3 mL), four times. Moisture in the organic layer thus obtained was removed using anhydrous MgSO$_4$, and organic solvents were removed using a rotary evaporator. The organic material thus obtained was separated by silica gel column chromatography (chloroform:n-hexane=1:1) to obtain a white solid final product. The solid product was 0.07 g, and the yield was analyzed as 21.7%.

Experimental Example 1: Manufacture of Organic Thin Film Transistor Device Using 4Bx Crosslinker Experimental Example 1-1: Manufacture of Bottom Gate Top Contact (BGTC) Organic Thin Film Transistor Device A heavily n-doped Si wafer having a SiO$_2$ layer with a thickness of about 300 nm was cleansed with acetone, isopropyl alcohol and water in order for about 10 minutes per each using an ultrasonic wave cleaner. The cleansed Si wafer was surface treated using ODTS. 5 mg of an organic semiconductor material, 1 wt % of 4Bx crosslinker and 1 mL of chloroform were added, and then stirred at room temperature to prepare a crosslinker composition. In a glove box in a nitrogen environment, the crosslinker composition was applied by spin coating on the Si wafer to manufacture a thin film. On the thin film, a photomask having a pattern was disposed, and the thin film was exposed to ultraviolet rays to crosslink the crosslinker composition. After that, an uncrosslinked portion was cleansed using chloroform in a spinning state using a spin coater. The substrate was stored in the glove box in a nitrogen environment for about 4 hours to remove remaining solvents. Gold was deposited using a vacuum deposition method to manufacture a source/drain electrode with a thickness of about 50 nm. Accordingly, the channel length and width of the electrode were about 100 μm and about 800 μm, respectively.

Experimental Example 1-2: Manufacture of Top Gate Bottom Contact (TGBC) Organic Thin Film Transistor and Logic Electronic Device Using 4Bx Crosslinker A PEN substrate was cleansed with acetone, isopropyl alcohol, and water in order for about 10 minutes per each using an ultrasonic wave cleaner. 50 mg of a solution in which silver-nanoparticles are dispersed, a 4Bx crosslinker (5 wt %) and 1 mL of anhydrous chloroform were stirred at room temperature to prepare a crosslinker composition. In a glove box in a nitrogen environment, the crosslinker composition was applied by spin coating on the PEN substrate to form a thin film. On the thin film, a photomask having a pattern was disposed, and the thin film was exposed to ultraviolet rays to crosslink the crosslinker composition. After that, an uncrosslinked portion was cleansed using chloroform in a spinning state using a spin coater. The substrate was heated in a vacuum oven of about 150° C. for about 8 hours. Accordingly, the thickness of a silver-nano electrode was about 72 nm, and the channel length and width of a source/drain electrode were about 100 μm and about 800 μm, respectively. 5 mg of an organic semiconductor material, 1 wt % of 4Bx crosslinker and 1 mL of chloroform were added, and then stirred at room temperature to prepare a crosslinker composition. On the substrate on which an electrode was patterned, the crosslinker composition was applied by spin coating to form a thin film. On the thin film, a photomask having a pattern was disposed, and the thin film was exposed to ultraviolet rays to crosslink the crosslinker composition. After that, an uncrosslinked portion was cleansed using chloroform in a spinning state using a spin coater. The substrate was stored in a glove box in a nitrogen environment for about 4 hours to remove remaining solvents. In this case, in case of a logic electronic device, after performing a patterning process of a p-type polymer semiconductor as the organic semiconductor material, a solution obtained by adding 5 mg of an n-type organic semiconductor material, 1 wt % of 4Bx and 1 mL of chloroform and stirring, was applied by spin coating to manufacture a thin film. On the thin film, a photomask was disposed, and the thin film was exposed to ultraviolet rays to crosslink. An uncrosslinked portion was cleansed using chloroform in a spinning state using a spin coater, and the substrate was stored in a glove box in a nitrogen environment for about 4 hours to remove remaining solvents. Then, a solution obtained by dissolving 70 mg of PMMA and 3.5 mg of a 4Bx crosslinker in 1 mL of n-butyl acetate was applied by spin coating to manufacture a thin film, and the thin film was exposed to ultraviolet rays to crosslink. After drying in a vacuum oven at about 80° C. for about 6 hours, the thickness of a polymer insulating layer was about 482 nm. On the polymer insulating layer, a gate electrode thin film was manufacture by the same method as the manufacturing method of the silver-nano source/drain (S/D) and crosslinked to manufacture an organic thin film transistor and a logic electronic device having a pattern.

Experimental Example 2: Manufacture of Organic Light-Emitting Diode Using 4Bx Crosslinker A substrate of a glass on which indium tin oxide (ITO) was deposited was cleansed with acetone and isopropyl alcohol in order for 10 minutes per each using an ultrasonic wave cleaner. On the substrate, poly(3,4-ethylenedioxythiophene) polystyrene sulfonate (PEDOT:PSS) was applied by spin coating (about 4,000 rpm, about 40 seconds) to form a polymer thin film. The polymer thin film was heated on a hot plate at about 110° C. for about 5 minutes and at about 180° C. for about 30 minutes, and then, dried in a glove box in a nitrogen environment at about 120° C. for about 15 minutes. In a separate glove box in the same nitrogen environment, a super yellow light-emitting polymer solution (7 mg/mL) was prepared using cyclohexanone as a solvent and stirring at about 110° C. A 4Bx solution (7 mg/mL) was prepared using cyclohexanone as a solvent and stirring at room temperature. The super yellow light-emitting polymer solution and the 4Bx solution were mixed in a mass ratio of about 99.9:0.1 to prepare a mixture. On the PEDOT:PSS thin film, the mixture was applied by spin coating (about 2,000 rpm, about 60 seconds) and exposed to ultraviolet rays in a glove box in a nitrogen environment to crosslink. In this case, a portion of the super yellow thin film was exposed by using a photomask to induce partial crosslinking of the thin film. A pure cyclohexanone solution was applied on the entire substrate and then spin coating (about 4,000 rpm, about 20 seconds) was performed to cleanse an uncrosslinked portion, twice. Through this, a super yellow polymer pattern may be formed. By using a hot plate in a glove box, the substrate was dried at about 180° C. for about 12 hours. A shadow mask having a pattern was disposed on the substrate, and lithium fluoride of about 2 nm and aluminum of about 150 nm were deposited in order using a vacuum deposition apparatus to manufacture an organic light-emitting diode.

Experimental Example 3: Manufacture of Quantum Dot Light-Emitting Diode Using 4Bx Crosslinker A substrate of a glass on which indium tin oxide (ITO) was deposited was cleansed with acetone and isopropyl alcohol in order for 10 minutes per each using an ultrasonic wave cleaner. On the substrate, poly(3,4-ethylenedioxythiophene) polystyrene sulfonate (PEDOT:PSS) thin film was coated (about 4,000 rpm, about 40 seconds) as a hole injection layer using a spin coater and then, was heated on a hot plate at about 110° C. for 5 minutes and at about 180° C. for about 30 minutes and additionally dried in a glove box in a nitrogen environment at about 120° C. for about 15 minutes. For efficient hole injection into a quantum dot, on the substrate coated with PEDOT:PSS, poly(N,N'-bis-4-butylphenyl-N,N'-bisphenyl)benzidine (poly-TPD) was coated (about 2,000 rpm, about 30 s) as a hole transport layer and dried at about 140° C. for about 30 minutes. An InP/ZnSeS core shell quantum dot solution and a 4Bx crosslinker solution dispersed in toluene in the same concentration were mixed in a ratio of about 0.5 wt % and applied by spin coating on the poly-TPD layer to form thin films. On the InP/ZnSeS quantum dot thin film, ultraviolet rays were irradiated to induce the crosslinking reaction of the ligand at the surface of the quantum dot and the 4Bx crosslinker for the gelation of the quantum dot thin film. In this process, the quantum dot thin film was partially crosslinked using a patterned shadow mask, and an uncrosslinked portion was cleansed with a toluene solvent to form a quantum dot pattern. On the crosslinked quantum dot thin film, a thin film of zinc oxide (ZnO) nanoparticles was formed (about 2,000 rpm, about 60 s) as an electron transport layer, and drying was performed at about 90° C. for about 30 minutes. An aluminum (Al) electrode of about 150 nm was deposited using a thermal deposition apparatus to manufacture a quantum dot light-emitting diode.

Figure 4:
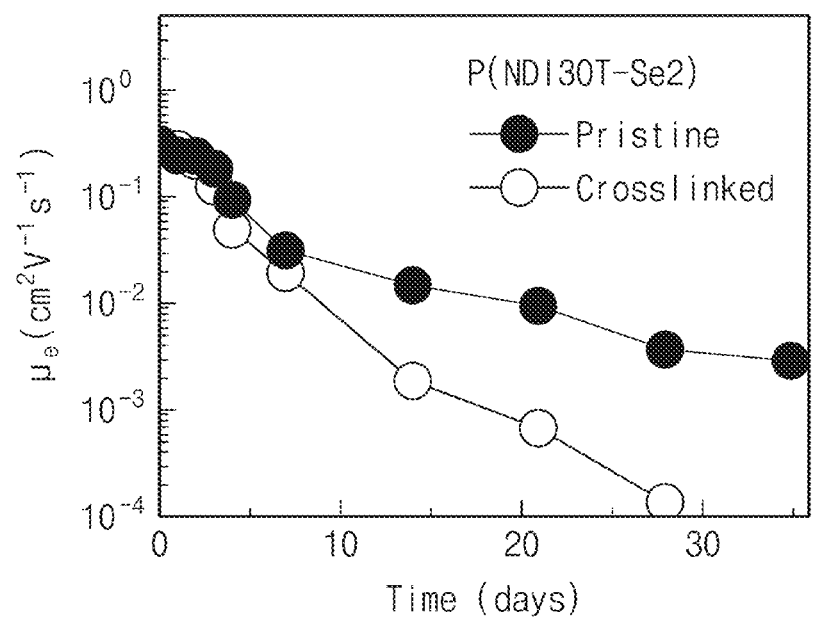
FIG. 4 shows evaluation results on the stability of electronic devices manufactured according to embodiments of the inventive concept.

Experimental Example 4: Evaluation of Stability of Organic Thin Film Transistor Device Using 4Bx Crosslinker By using P(DPP2DT-TVT) and a 4Bx crosslinker, the stability of the organic thin film transistor manufactured according the manufacturing method of Experimental Example 1 was evaluated. Particularly, the inspected results of the change of hole transport performance in accordance with time is shown in FIG. 4. It could be confirmed that the organic thin film transistor (crosslinked) to which the 4Bx crosslinker was added maintained hole transport performance for a long time with the lapse of time when compared with the organic thin film transistor (pristine) to which the 4Bx crosslinker was not added. That is, it was confirmed that the stability of the organic thin film transistor (crosslinked) to which the 4Bx crosslinker was added was improved further when compared with the organic thin film transistor (pristine) to which the 4Bx crosslinker was not added.

Figure 5A:
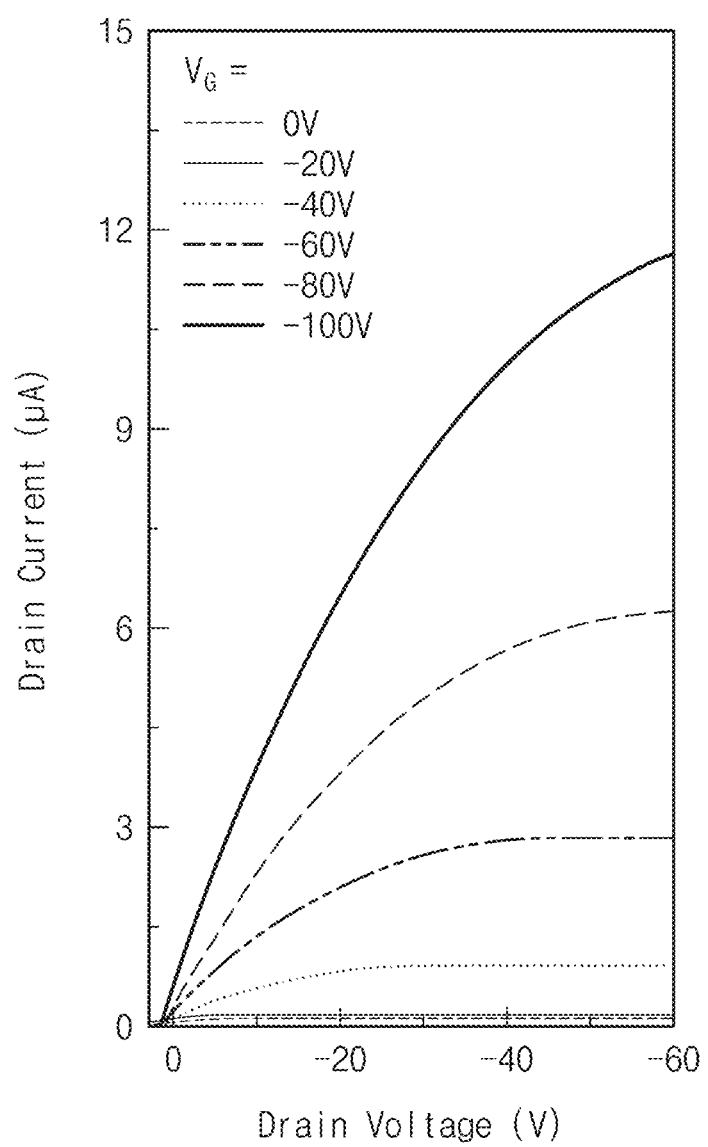
FIG. 5A to FIG. 5C show evaluation results on the electric properties of electronic devices manufactured according to embodiments of the inventive concept.
Figure 5B:
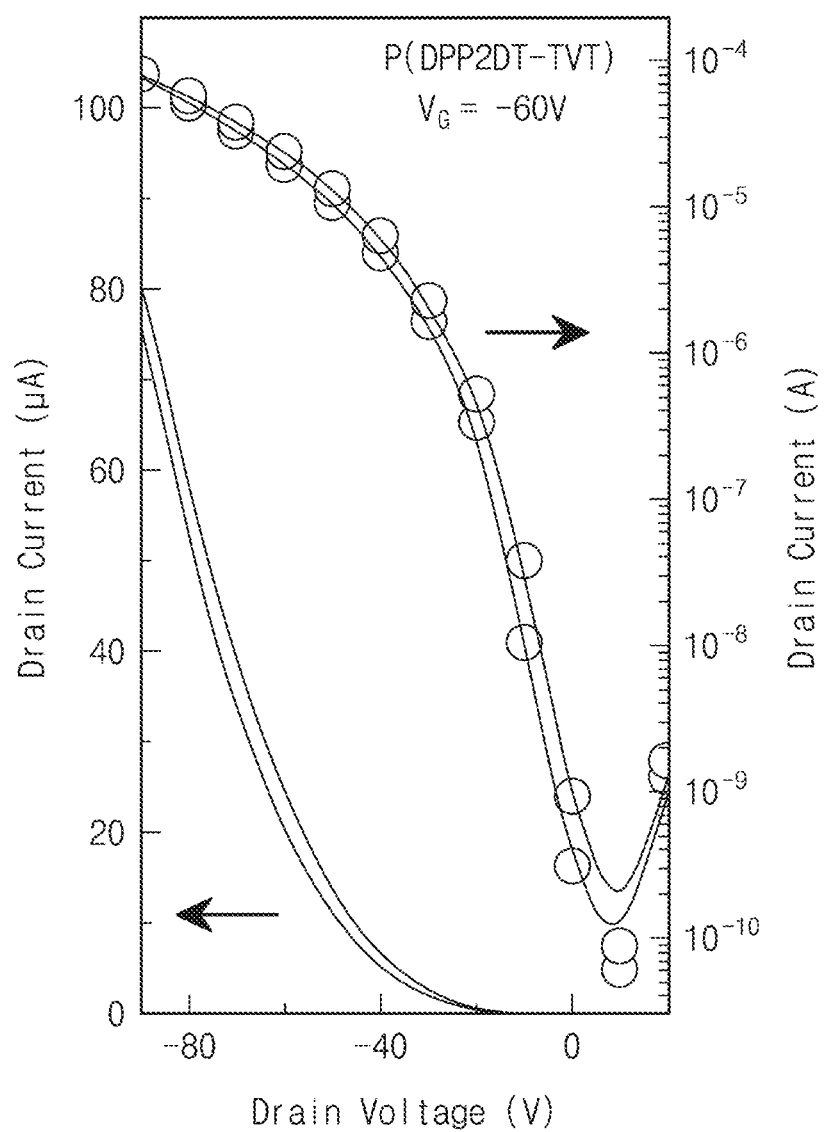
Figure 5C:
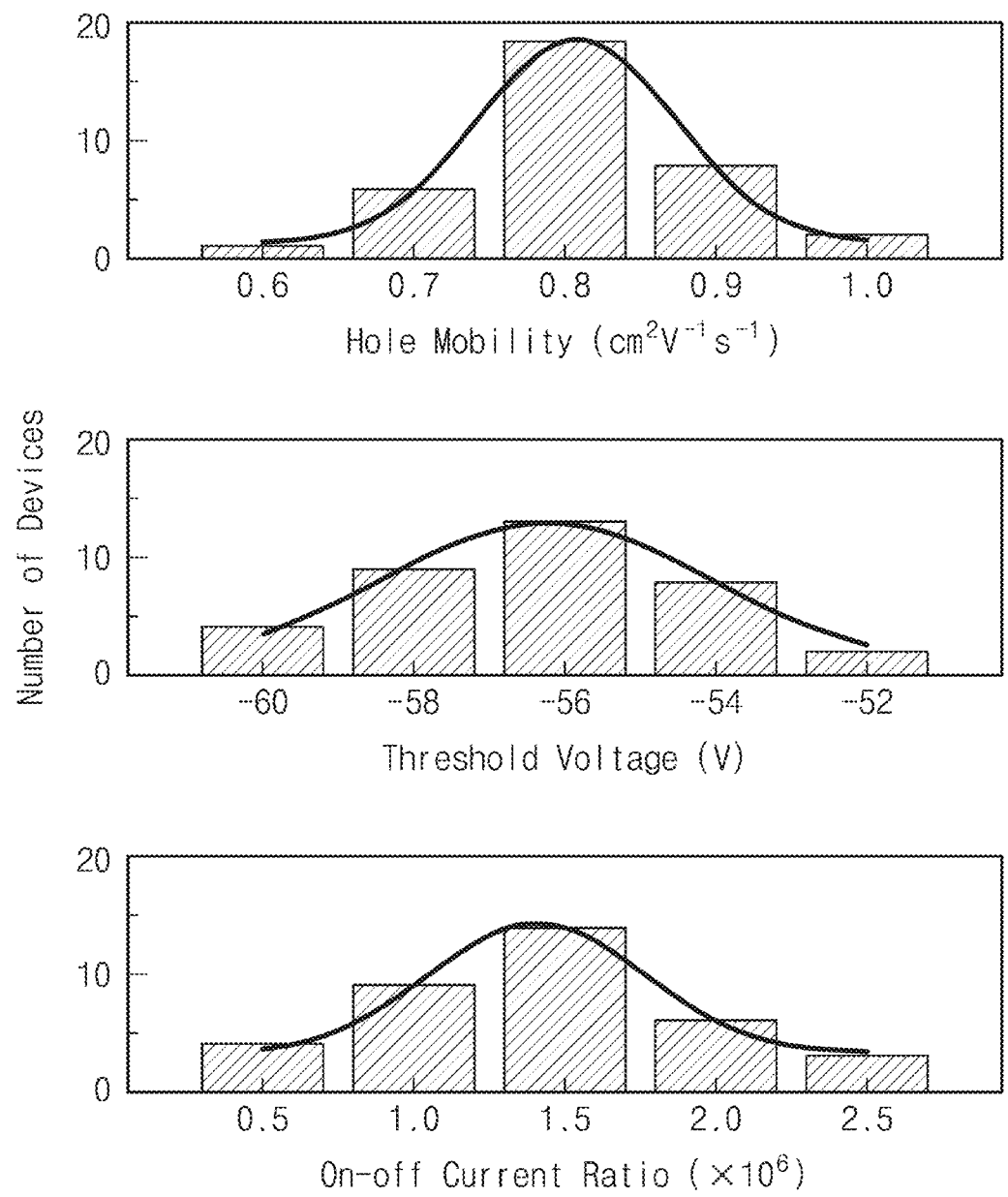

Experimental Example 5: Evaluation of Electrical Properties of Organic Thin Film Transistor Device Using 4Bx Crosslinker By using P(DPP2DT-TVT) and a 4Bx crosslinker, the electrical properties of the organic thin film transistor manufactured according to the manufacturing method of Experimental Example 1 were evaluated. The evaluation results on the output properties of the organic thin film transistor at six different gate voltages (VG) are shown in FIG. 5A. The evaluation results on the transfer properties of the organic thin film transistor at a fixed drain voltage ($V_D$) of about −60 V are shown in FIG. 5B. The evaluation results on the hole transport capacity, threshold voltage and on/off ratio of the organic thin film transistor are shown in FIG. 5C.

Figure 6A:
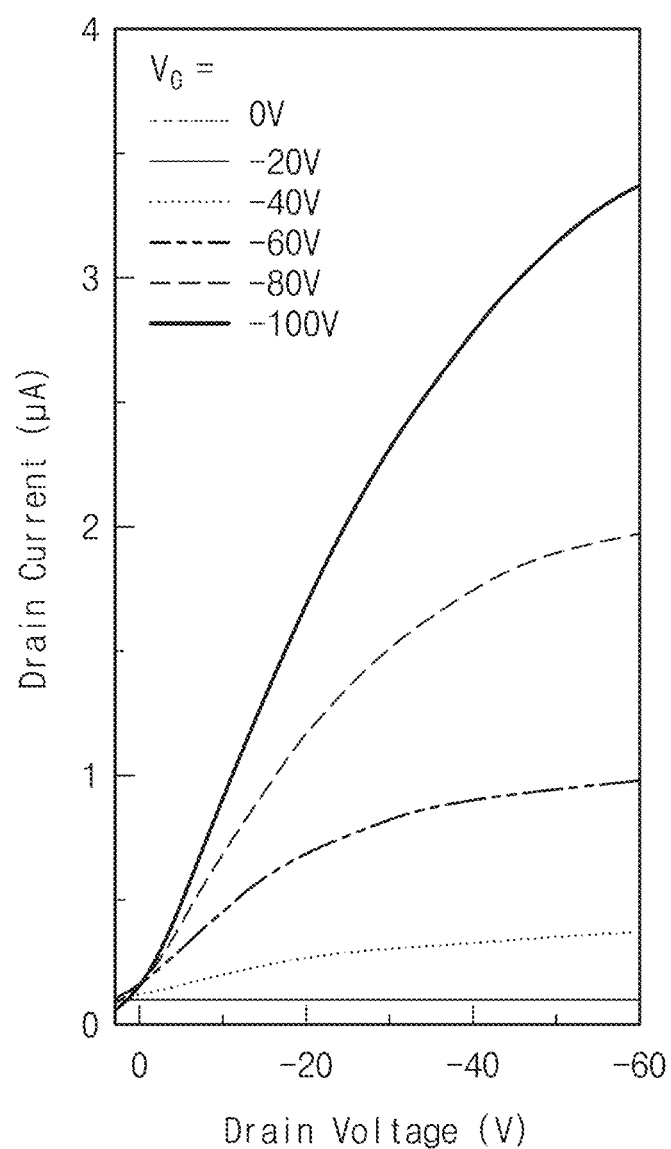
FIG. 6A to FIG. 6C show evaluation results on the electric properties of electronic devices manufactured according to embodiments of the inventive concept.
Figure 6B:
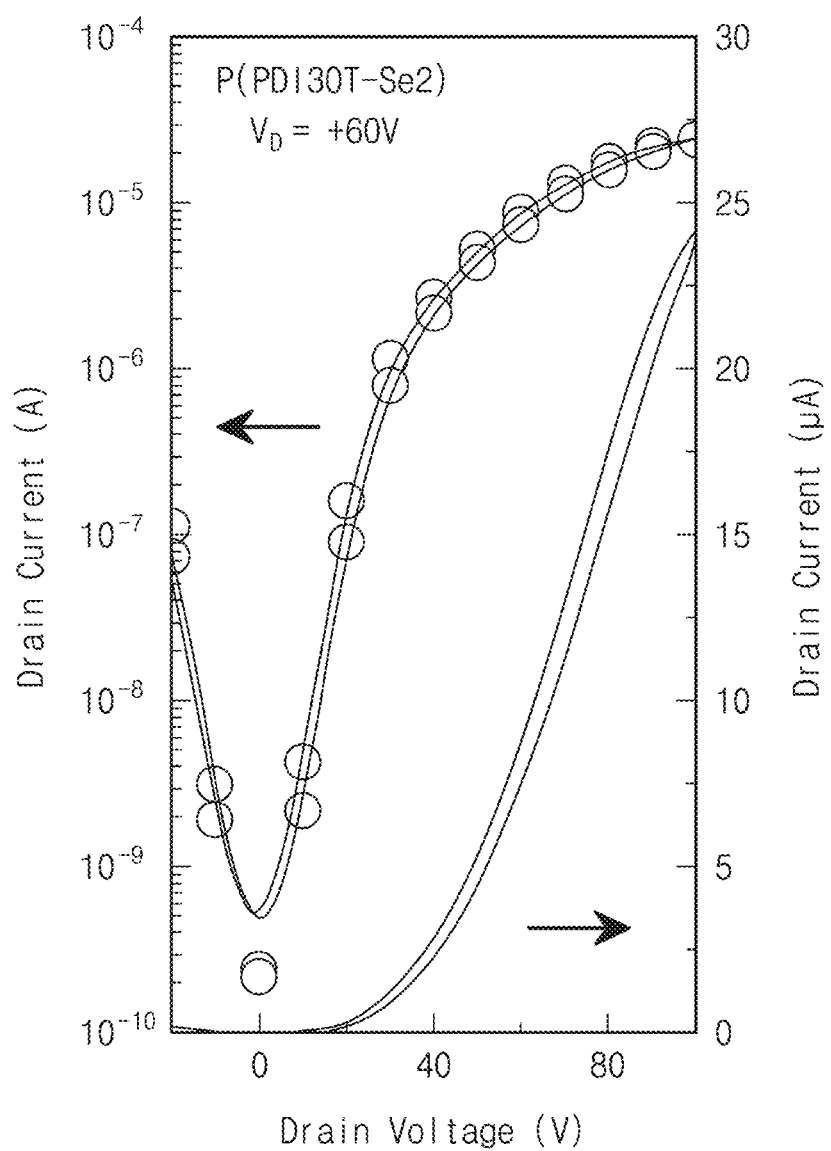
Figure 6C:
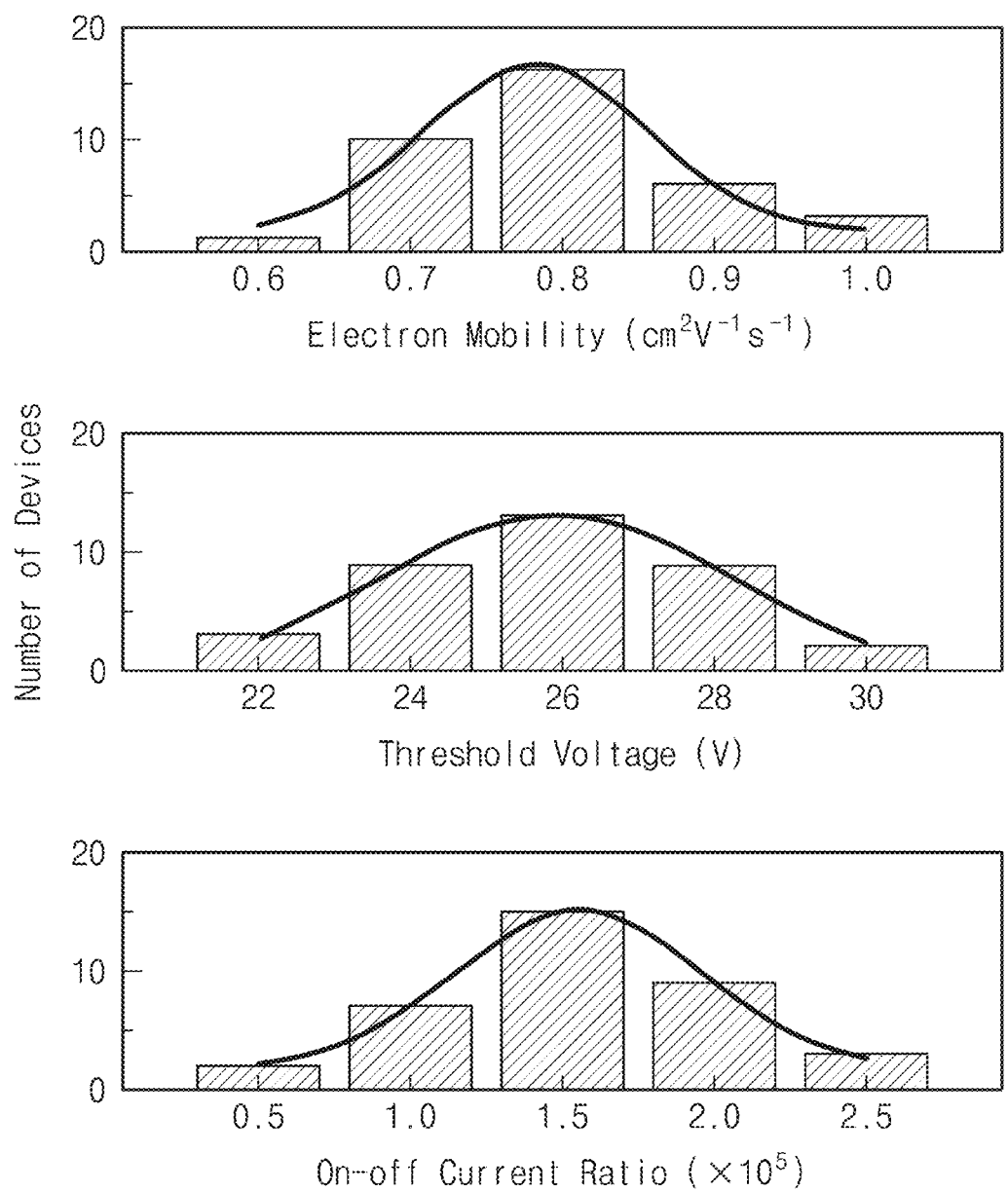

By using P(NDI3OT-Se2) and a 4Bx crosslinker, the electrical properties of the organic thin film transistor manufactured according to the manufacturing method of Experimental Example 1 were evaluated. The evaluation results on the output properties of the organic thin film transistor at six different gate voltages (VG) are shown in FIG. 6A. The evaluation results on the transfer properties of the organic thin film transistor at a fixed drain voltage ($V_D$) of about +60 V are shown in FIG. 6B. The evaluation results on the hole transport capacity, threshold voltage and on/off ratio of the organic thin film transistor are shown in FIG. 6C.

By using various semiconductor materials and a 4Bx crosslinker, the electrical properties of the organic thin film transistors manufactured according to the manufacturing method of Experimental Example 1 were evaluated. The evaluation results on the hole transport capacity, threshold voltage and on/off ratio of the organic thin film transistors are shown in Table 1 below. The numerical values in bold mean the maximum mobility.

TABLE 1

| Semiconductor | Carrier mobility ($cm^2V^{-1}s^{-1}$) | | Carrier type | On-off current ratio | Threshold voltage |
|---|---|---|---|---|---|
| P(DPP2DT-TVT)   | 0.81(±0.18)   | 1.03  | p-type | 1.6(±0.8) × $10^6$ | −56(±4) V |
| P(DPP2DT-F2T2)  | 0.72(±0.21)   | 0.94  | p-type | 2.5(±0.5) × $10^6$ | −74(±5) V |
| P(DPP2DT-T2)    | 0.25(±0.09)   | 0.35  | p-type | 1.4(±1.1) × $10^6$ | −60(±3) V |
| PTB7-Th         | 0.005(±0.001) | 0.007 | p-type | 4.1(±1.8) × $10^5$ | −42(±6) V |
| P(NDI3OT-Se2)   | 0.15(±0.09)   | 0.24  | n-type | 1.5(±0.9) × $10^5$ | 26(±4) V  |
| P(NDI2OD-F2T2)  | 0.10(±0.03)   | 0.13  | n-type | 2.1(±1.1) × $10^6$ | 47(±7) V  |
| P(NDI2OD-Se2)   | 0.14(±0.05)   | 0.19  | n-type | 6.1(±0.4) × $10^5$ | 74(±8) V  |
| P(NDI3OT-Se)    | 0.14(±0.05)   | 0.21  | n-type | 2.8(±0.8) × $10^5$ | 28(±4) V  |

Through the evaluation results on the electrical properties, it could be confirmed that by manufacturing an electronic device using the crosslinker composition of the inventive concept, the manufacturing process may be simplified, and at the same time, the damage of the constituent elements of the electronic device may be prevented, and accordingly, the electrical properties of the electronic device may be improved.

Experimental Example 6: Manufacture of Top Gate Bottom Contact (TGBC) Organic Thin Film Transistor and Logic Electronic Device Using 6Bx A PEN substrate was cleansed with acetone, isopropyl alcohol and water, in order for about 10 minutes per each using an ultrasonic wave cleaner. A source/drain electrode (Cr/Au) was deposited by a thermal deposition method on the PEN substrate using a shadow mask. Accordingly, the thickness of the Cr/Au electrode thus formed was about 3/17 nm, and the channel length and width of the source/drain electrode were about 100 μm and about 800 μm, respectively. 4.95 mg of an organic semiconductor material, 0.05 mg of a 6Bx crosslinker and 1 mL of chloroform were added and stirred at room temperature to prepare a crosslinker composition. On the substrate on which an electrode was formed, the crosslinker composition was applied by spin coating (about 1,000 rpm, about 30 s) to form a thin film. On the thin film, a photomask having a pattern was disposed, and the thin film was exposed to ultraviolet rays to crosslink the crosslinker composition. Then, by using a spin coater, an uncrosslinked portion was cleansed with chloroform in a spinning state. The substrate was stored in a glove box in a nitrogen environment for about 4 hours to remove remaining solvents. In this case, in case of a logic electronic device, after performing a patterning process of the p-type polymer semiconductor as the organic semiconductor material, a solution obtained by adding 4.95 mg of an n-type organic semiconductor material, 0.05 mg of 6Bx and 1 mL of chloroform and stirring was applied by spin coating (about 1,000 rpm, about 30 s) to form a thin film. On the thin film, a photomask was disposed, and the thin film was exposed to ultraviolet rays for crosslinking. Then, by using a spin coater, an uncrosslinked portion was cleansed with chloroform in a spinning state and stored in a glove box in a nitrogen environment for about 4 hours to remove remaining solvents. After that, a solution obtained by dissolving 9.7 mg of PMMA and 0.3 mg of a 6Bx crosslinker in 1 mL of n-butyl acetate was applied by spin coating (about 1,000 rpm, about 60 s) to form a thin film, and the thin film was exposed to ultraviolet rays for crosslinking. After drying in a vacuum oven of about 80° C. for about 6 hours, and a polymer insulating layer had a thickness of about 52 nm. On the polymer insulating layer, Al used as a gate electrode was deposited to a thickness of about 40 nm to manufacture an organic thin film transistor.

Figure 7A:
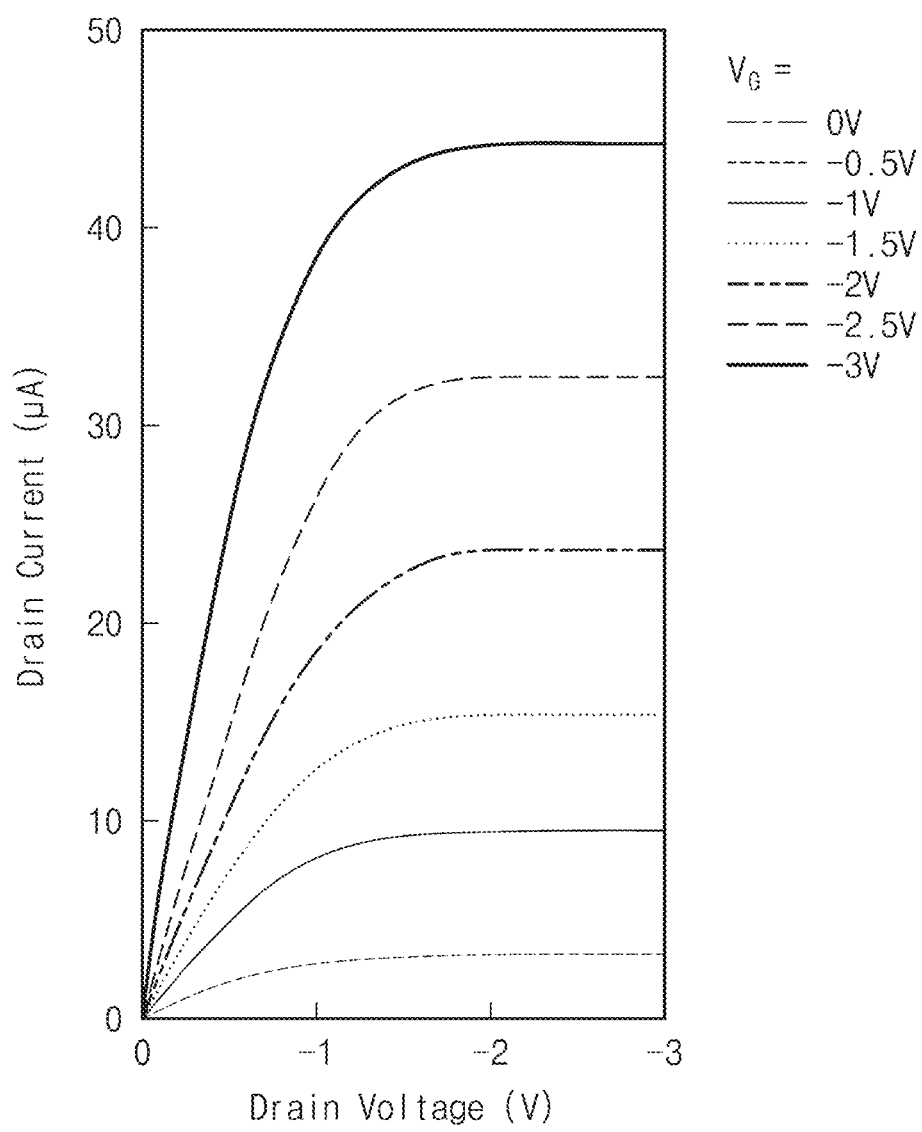
FIG. 7A to FIG. 7C show evaluation results on the electric properties of organic thin film transistors manufactured according to embodiments of the inventive concept.
Figure 7B:
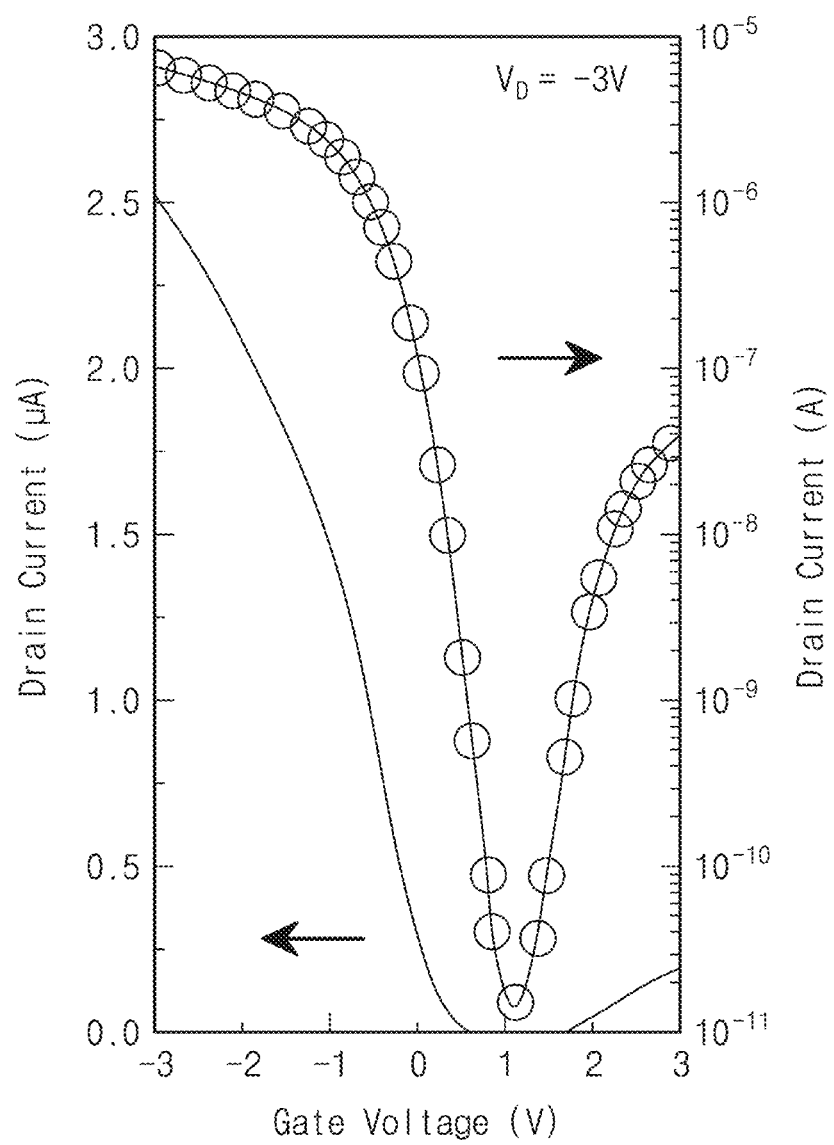
Figure 7C:
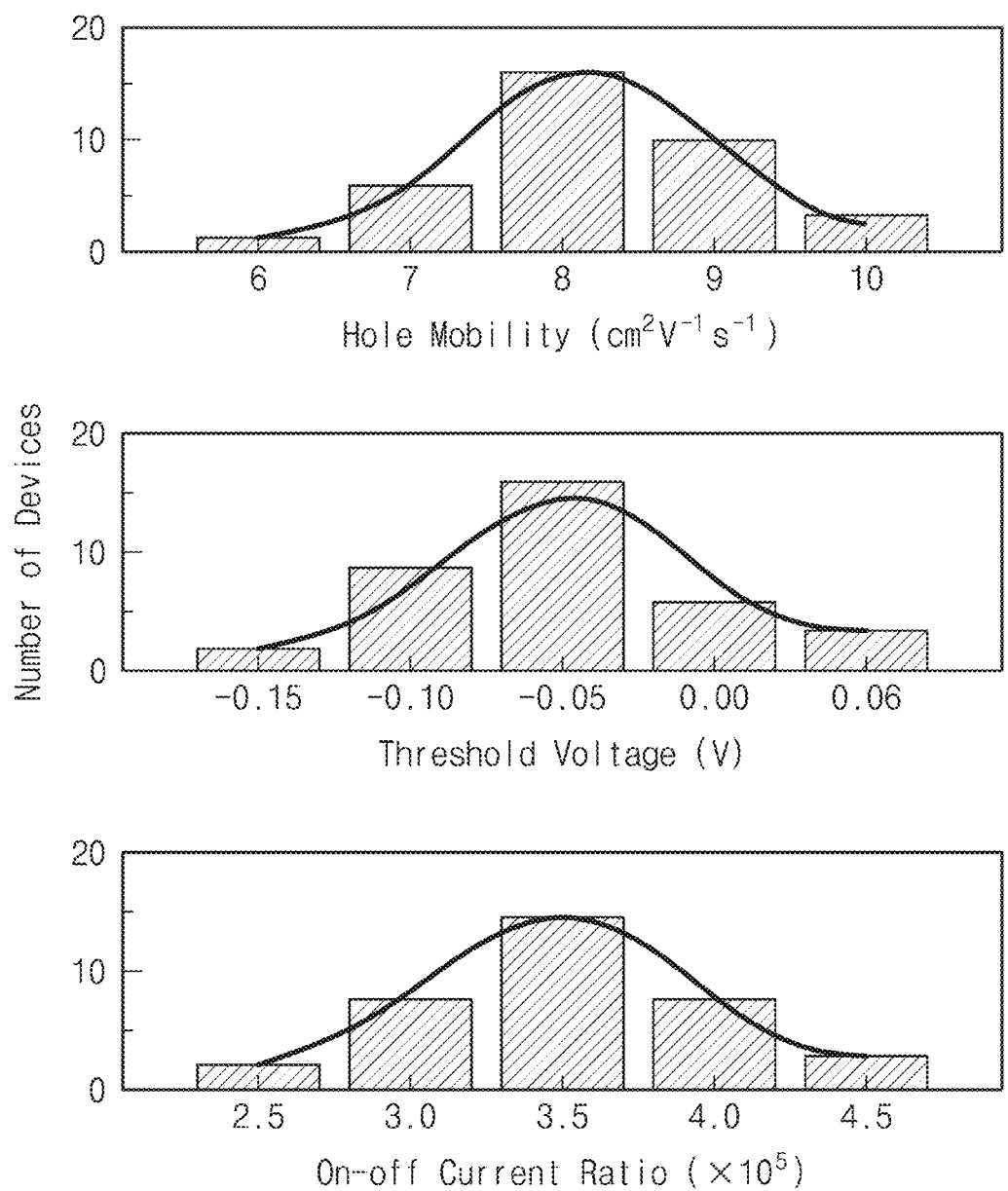

Experimental Example 7: Evaluation of Electrical Properties of Organic Thin Film Transistor Using 6Bx By using P(DPP2DT-TT), a 6Bx crosslinker and a PMMA insulating material, the electrical properties of the organic thin film transistor manufactured according to the manufacturing method of Experimental Example 6 were evaluated. The evaluation results on the output properties of the organic thin film transistor at six different gate voltages (VG) are shown in FIG. 7A. The evaluation results on the transfer properties of the organic thin film transistor at a fixed drain voltage ($V_D$) of about −3 V are shown in FIG. 7B. The evaluation results on the hole transport capacity, threshold voltage and on/off ratio of the organic thin film transistor are shown in FIG. 7C.

Figure 8A:
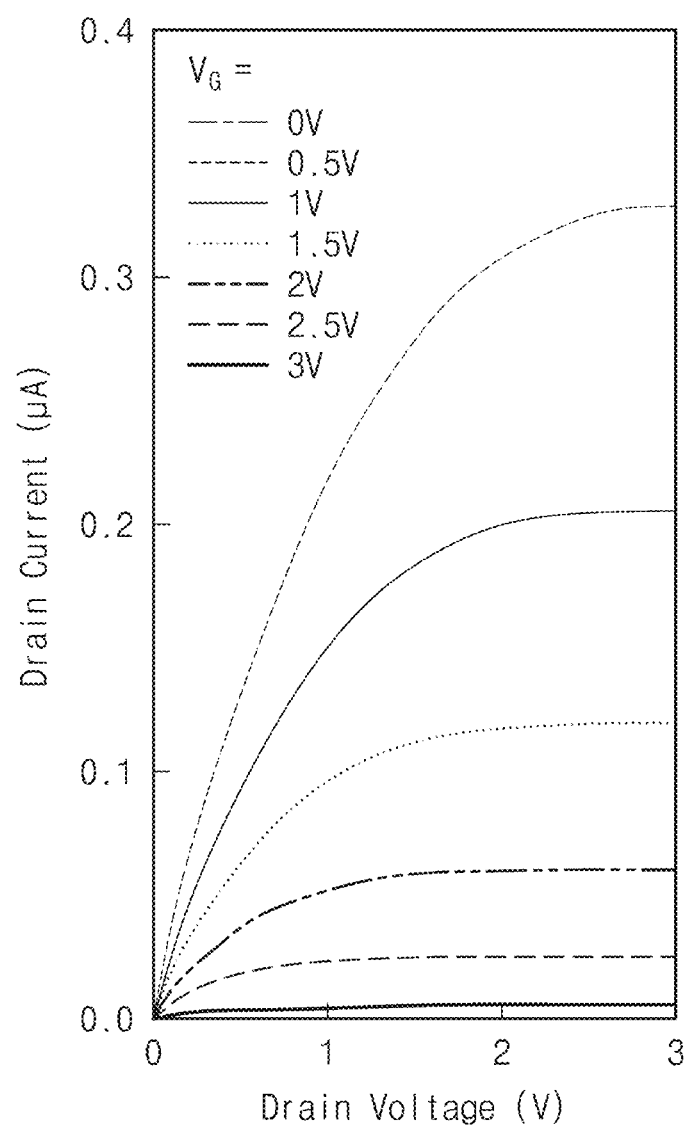
FIG. 8A to FIG. 8C show evaluation results on the electric properties of organic thin film transistors manufactured according to embodiments of the inventive concept.
Figure 8B:
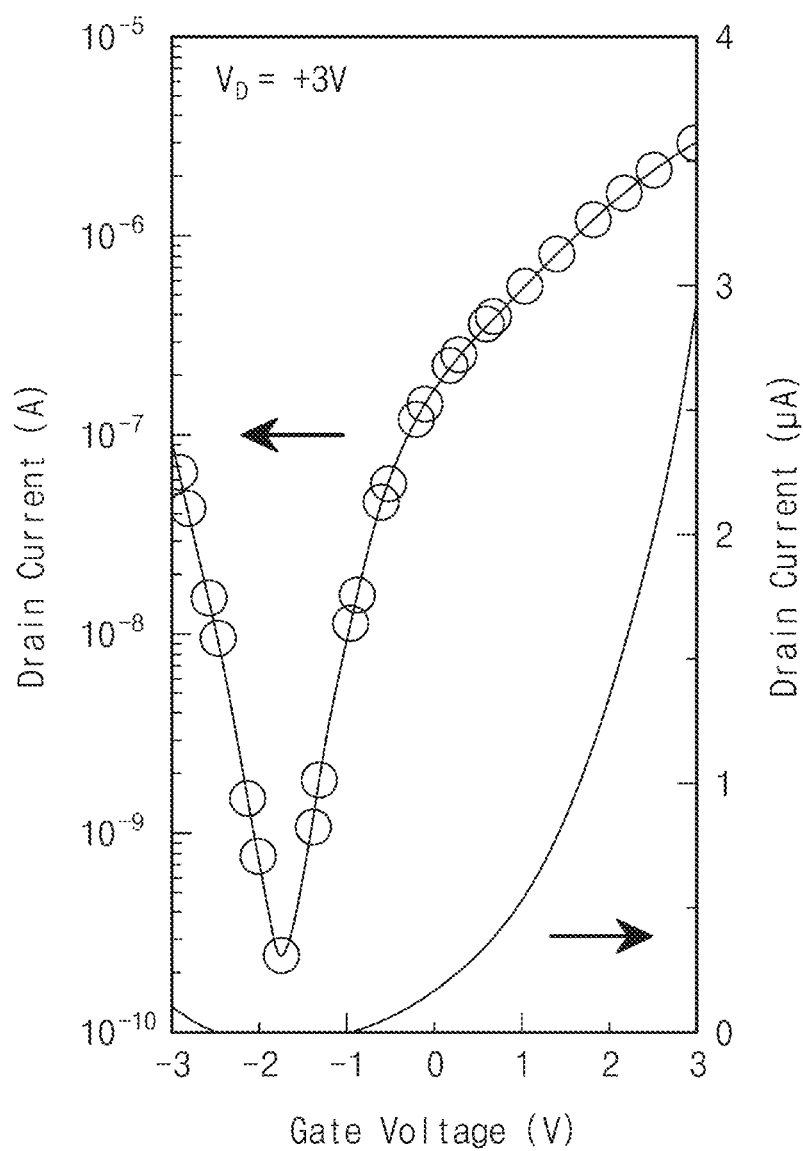
Figure 8C:
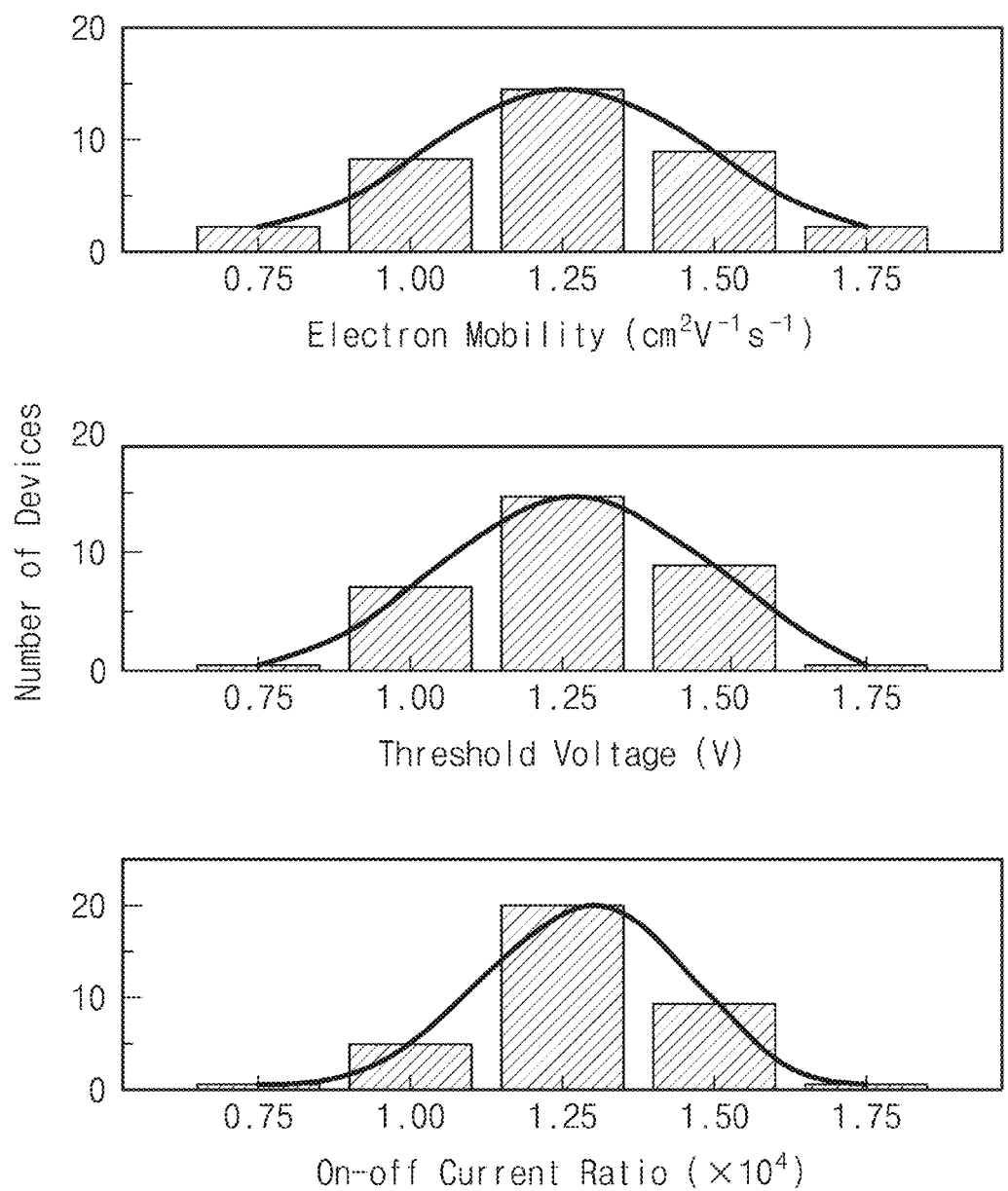

By using P(NDI3OT-Se2), a 6Bx crosslinker, and a PMMA insulating material, the electrical properties of the organic thin film transistor manufactured according to the manufacturing method of Experimental Example 6 were evaluated. The evaluation results on the output properties of the organic thin film transistor at six different gate voltages (VG) are shown in FIG. 8A. The evaluation results on the transfer properties of the organic thin film transistor at a fixed drain voltage ($V_D$) of about +3 V are shown in FIG. 8B. The evaluation results on the hole transport capacity, threshold voltage and on/off ratio of the organic thin film transistor are shown in FIG. 8C.

By using various semiconductor materials and a 6Bx crosslinker, the electrical properties of the organic thin film transistors manufactured according to the manufacturing method of Experimental Example 6 were evaluated. The evaluation results on the hole transport capacity, threshold voltage and on/off ratio of the organic thin film transistors are shown in Table 2 below. The numerical values in bold mean the maximum mobility.

TABLE 2

| Semiconductor | Carrier mobility ($cm^2V^{-1}s^{-1}$) | | Carrier type | On-off current ratio | Threshold voltage |
|---|---|---|---|---|---|
| P(DPP2DT-TT) | 8.8(±1.9) | 10.5 | p-type | 3.5(±1.1) × $10^5$ | −0.05 (±0.11) V |
| P(NDI3OT-Se2) | 1.35(±0.1) | 1.75 | n-type | 2.0(±1.1) × $10^4$ | 1.25(±0.48) V |

Through the evaluation results on the electrical properties, it could be confirmed that according to the manufacture of an electronic device using the crosslinker composition of the inventive concept, the manufacturing process may be simplified and at the same time, the damage of the constituent elements of the electronic device may be prevented, and accordingly, the electrical properties of the electronic device may be improved. Particularly, the thickness of a PMMA layer may be reduced further by using 6Bx, the improving properties of the mobility by about twice to seven times and the reducing properties of the threshold voltage by about 20 times or more could be secured at the same time.

According to the inventive concept, a photoresist layer for forming a pattern or manufacturing an electronic device may not be necessary. Accordingly, a manufacturing process may be simplified, and at the same time, the damage of the configuration elements of an electronic device may be prevented. Further, the electric properties and stability of an electronic device manufactured using a three-dimensional crosslinker composition may be improved.

Although the embodiments of the present invention have been described, it is understood that the present invention should not be limited to these embodiments but various changes and modifications can be made by one ordinary skilled in the art within the spirit and scope of the present invention as hereinafter claimed.

What is claimed is:

1. A crosslinker composition comprising a compound represented by any one selected from the following Formula 3-4 to Formula 3-9:

[Formula 3-4]

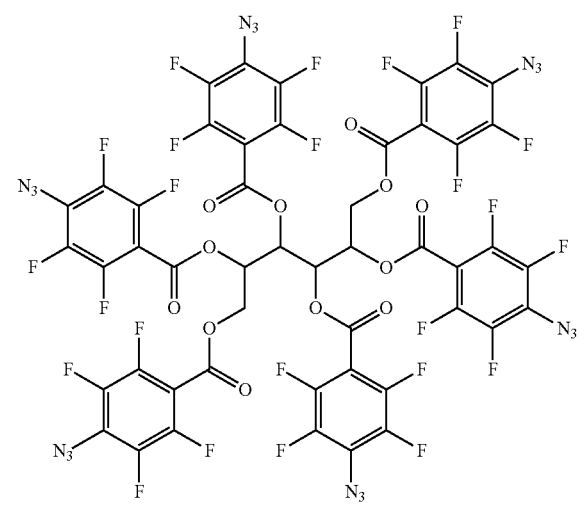

-continued

[Formula 3-5]

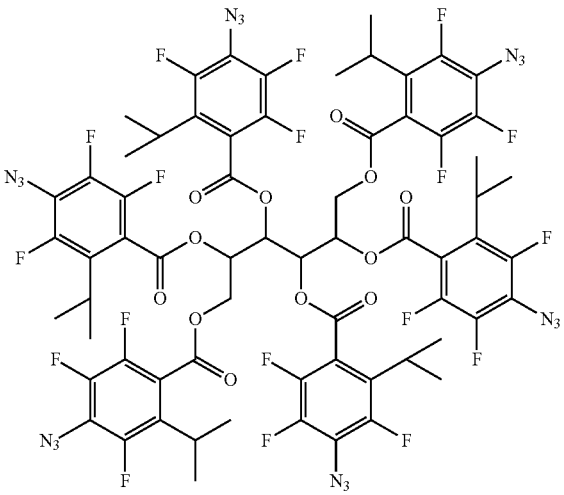

[Formula 3-6]

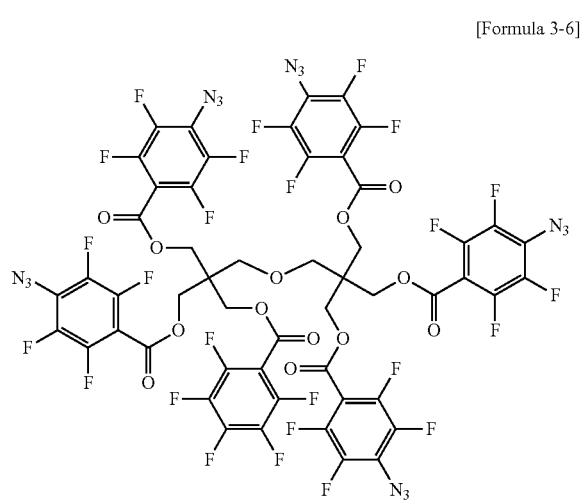

[Formula 3-7]
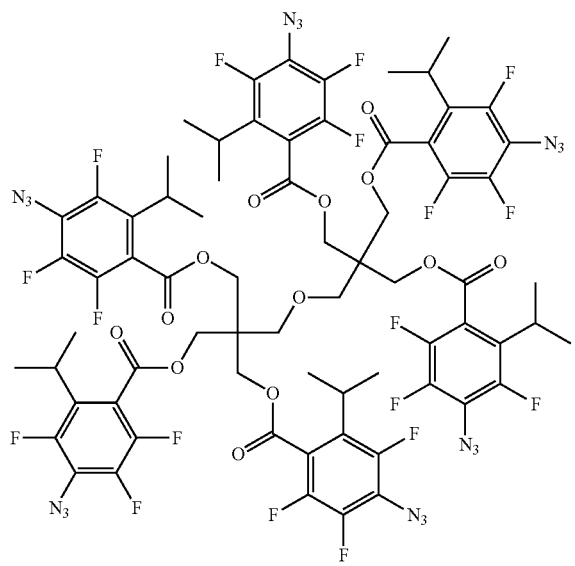
[Formula 3-8]
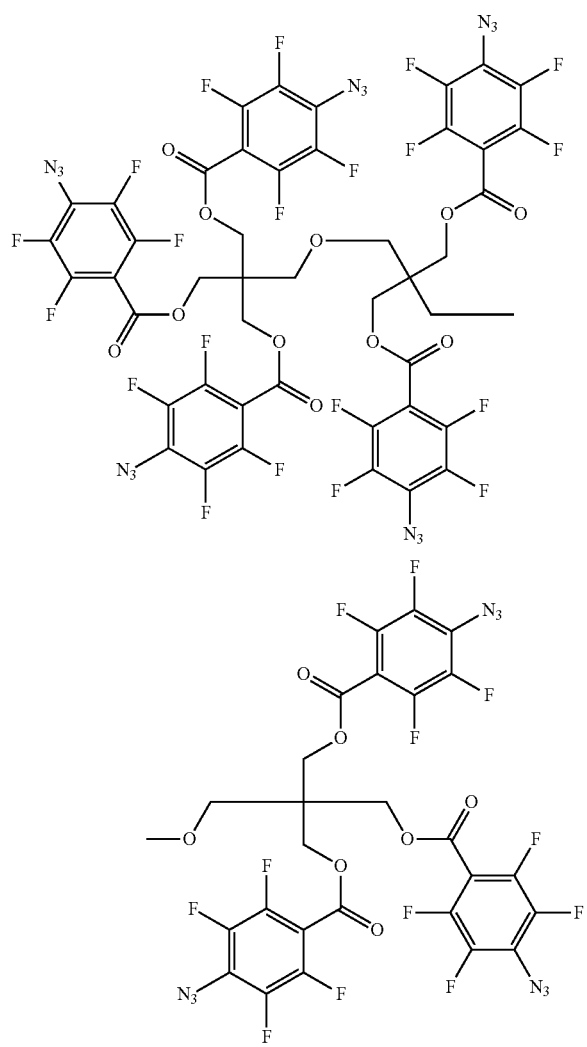
[Formula 3-9]
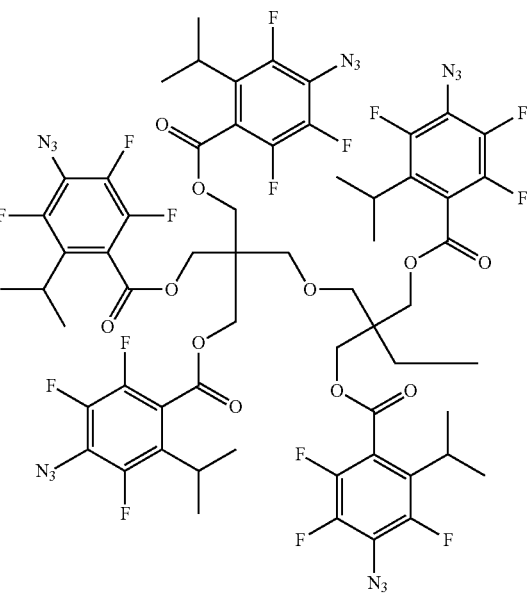
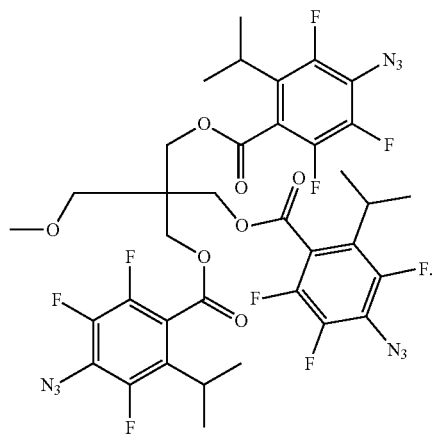
2. A method of manufacturing an electronic device, the method comprising:
   applying a crosslinker composition comprising a compound represented by any one selected from the following Formula 3-4 to Formula 3-9 on a substrate to form a lower layer; and
   patterning the lower layer,

[Formula 3-4]
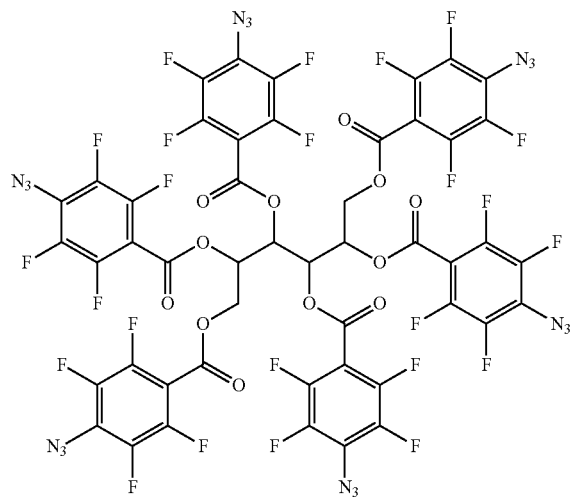
[Formula 3-5]
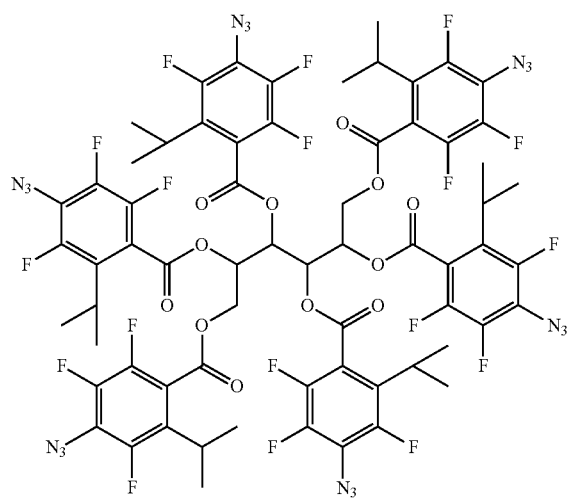
[Formula 3-6]
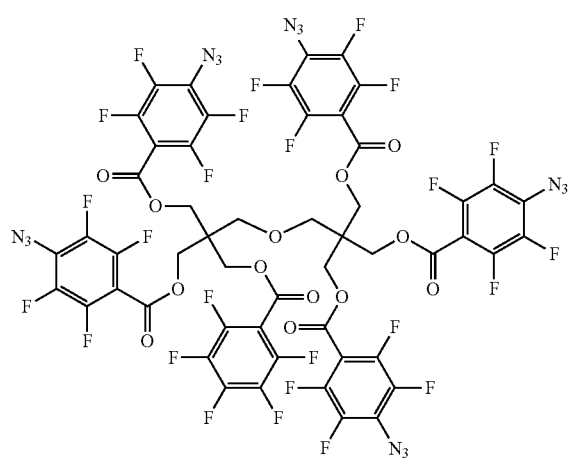

[Formula 3-7]
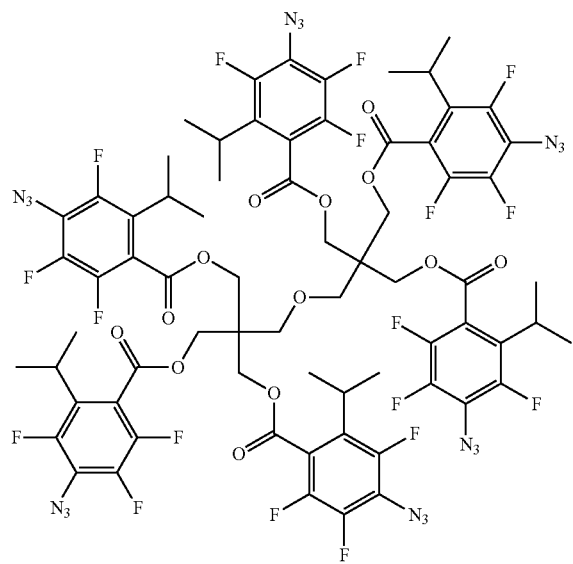
[Formula 3-8]
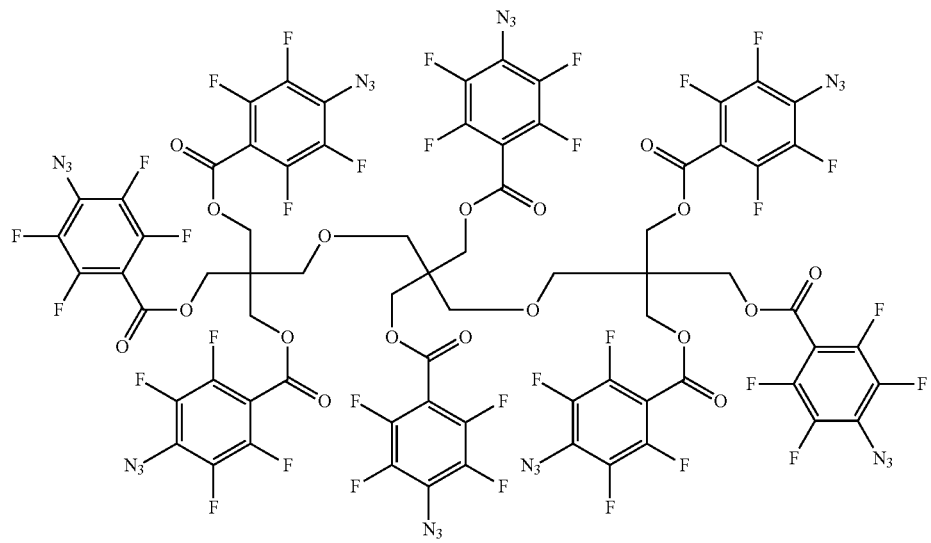

-continued

[Formula 3-9]

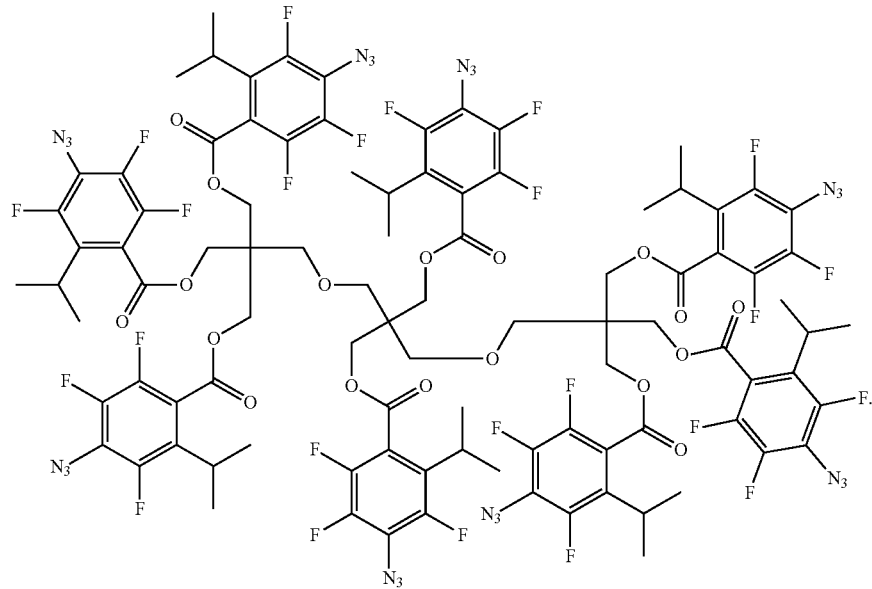

3. The method of manufacturing an electronic device of claim 2, wherein the patterning of the lower layer comprises:
disposing a photomask on the lower layer;
irradiating light onto the photomask; and
removing a portion of the lower layer.

4. The method of manufacturing an electronic device of claim 3, wherein the irradiating of light onto the photomask is direct irradiating of light onto a portion of the lower layer.

* * * * *